(12) United States Patent
Bobey et al.

(10) Patent No.: US 7,698,765 B2
(45) Date of Patent: Apr. 20, 2010

(54) PATIENT SUPPORT

(75) Inventors: John A. Bobey, Daniel Island, SC (US); Gregory W. Branson, Batesville, IN (US); Colin Clarke, Victoria (CA); Rachel Hopkins King, Lawrenceburg, IN (US); David Lokhorst, Victoria (CA); Eric R. Meyer, Greensburg, IN (US); Jonathan H. Mueller, Mt. Pleasant, SC (US); Todd P. O'Neal, Fairfield, OH (US); Robert Petrosenko, Daniel Island, SC (US); Stephen R. Schulte, Harrison, OH (US); Andrew F. Skinner, Bateville, IN (US); Michael Z. Sleva, Wyoming, OH (US); Sohrab Soltani, Charleston, SC (US); Richard B. Stacy, Daniel Island, SC (US); Daniel K. Stevens, Summerville, SC (US); Mayur Yermaneni, Cincinnati, OH (US)

(73) Assignee: Hill-Rom Services, Inc., Wilmington, DE (US)

(*) Notice: Subject to any disclaimer, the term of this patent is extended or adjusted under 35 U.S.C. 154(b) by 0 days.

(21) Appl. No.: 11/324,520

(22) Filed: Jan. 3, 2006

(65) Prior Publication Data

US 2006/0112489 A1 Jun. 1, 2006

Related U.S. Application Data

(63) Continuation of application No. 11/120,080, filed on May 2, 2005, now abandoned.

(60) Provisional application No. 60/567,215, filed on Apr. 30, 2004, provisional application No. 60/665,241, filed on Mar. 25, 2005, provisional application No. 60/665,141, filed on Mar. 25, 2005, provisional application No. 60/636,252, filed on Dec. 15, 2004, provisional application No. 60/608,013, filed on Sep. 8, 2004.

(51) Int. Cl.
    *A47C 27/10* (2006.01)
(52) U.S. Cl. .................. 5/713; 5/710; 5/655.3
(58) Field of Classification Search .............. 5/706, 5/710, 713, 655.3
    See application file for complete search history.

(56) References Cited

U.S. PATENT DOCUMENTS 779,576 A   1/1905  Berryman (Continued)

FOREIGN PATENT DOCUMENTS

CA   2 393 880 A1   1/2004

(Continued)

OTHER PUBLICATIONS

A Hill-Rom Solution, Acucair Continuous Airflow System. .Hill-Rom Company, Inc., Batesville, Indiana, 1998, 4 pgs.

(Continued)

*Primary Examiner*—Fredrick Conley
(74) *Attorney, Agent, or Firm*—Barnes & Thornburg LLP

(57) ABSTRACT

This disclosure describes certain exemplary embodiments of a patient support having a plurality of vertically-oriented or substantially can-shaped inflatable bladders. In one embodiment, the patient support includes a plurality of pressure sensors positioned underneath the bladders. In another embodiment, the patient support includes a support layer positioned above the vertical bladders. In still another embodiment, the patient support includes one or more filler portions that are selectable so that the patient support may conform to bed frames having different deck configurations.

13 Claims, 24 Drawing Sheets

U.S. PATENT DOCUMENTS

| | | |
|---|---|---|
| 800,967 A | 10/1905 | Young et al. |
| 1,121,277 A | 12/1914 | Mitchell |
| 1,332,933 A | 3/1920 | Sylvester |
| 1,758,546 A | 5/1930 | Wartmann |
| 1,772,310 A | 8/1930 | Hart |
| 1,969,554 A | 8/1934 | Gloudemans |
| 2,425,790 A | 8/1947 | Fletcher |
| 3,303,518 A | 2/1967 | Ingram |
| 3,428,973 A | 2/1969 | Hargest et al. |
| 3,492,988 A | 2/1970 | De Mare |
| 3,605,145 A | 9/1971 | Graebe |
| 3,639,927 A | 2/1972 | Munch |
| 3,656,478 A | 4/1972 | Swersey |
| 3,747,952 A | 7/1973 | Graebe |
| 3,748,835 A | 7/1973 | Yu et al. |
| 3,772,717 A | 11/1973 | Yuen et al. |
| 3,836,900 A | 9/1974 | Mansfield |
| 3,852,736 A | 12/1974 | Cook et al. |
| 3,868,604 A | 2/1975 | Curless et al. |
| 3,870,450 A | 3/1975 | Graebe |
| 3,903,878 A | 9/1975 | Spann |
| 3,931,654 A | 1/1976 | Spann |
| 3,938,205 A | 2/1976 | Spann |
| 3,939,829 A | 2/1976 | Spann |
| 3,946,451 A | 3/1976 | Spann |
| 3,978,530 A | 9/1976 | Amarantos |
| 3,991,414 A | 11/1976 | Moran |
| 3,999,235 A | 12/1976 | Mollura |
| 4,002,216 A | 1/1977 | Solow |
| 4,005,236 A | 1/1977 | Graebe |
| 4,020,482 A | 4/1977 | Feldl |
| 4,038,973 A | 8/1977 | Moore |
| 4,067,005 A | 1/1978 | Levy et al. |
| 4,108,170 A | 8/1978 | Spann |
| 4,114,620 A | 9/1978 | Moore et al. |
| 4,135,504 A | 1/1979 | Spann |
| 4,172,216 A | 10/1979 | O'Shea |
| 4,179,692 A | 12/1979 | Vance |
| 4,185,813 A | 1/1980 | Spann |
| 4,193,149 A | 3/1980 | Welch |
| 4,195,287 A | 3/1980 | McCoy et al. |
| 4,196,425 A | 4/1980 | Williams, Jr. et al. |
| 4,210,317 A | 7/1980 | Spann et al. |
| 4,214,326 A | 7/1980 | Spann |
| 4,220,984 A | 9/1980 | Truher et al. |
| 4,233,700 A | 11/1980 | Spann |
| 4,242,672 A | 12/1980 | Gault |
| 4,263,586 A | 4/1981 | Nicholas |
| 4,295,133 A | 10/1981 | Vance |
| 4,320,766 A | 3/1982 | Alihanka et al. |
| 4,327,714 A | 5/1982 | Spann |
| 4,347,633 A | 9/1982 | Gammons et al. |
| 4,378,476 A | 3/1983 | Nicholas |
| 4,418,514 A | 12/1983 | Spann |
| 4,433,678 A | 2/1984 | Spann |
| 4,435,864 A | 3/1984 | Callaway |
| 4,448,228 A | 5/1984 | Hashimoto et al. |
| 4,471,952 A | 9/1984 | Spann |
| 4,477,935 A | 10/1984 | Griffin |
| 4,482,138 A | 11/1984 | Spann |
| 4,483,029 A | 11/1984 | Paul |
| 4,483,663 A | 11/1984 | Myers |
| 4,525,885 A | 7/1985 | Hunt |
| 4,527,298 A | 7/1985 | Moulton |
| 4,539,560 A | 9/1985 | Fleck et al. |
| 4,541,135 A | 9/1985 | Karpov |
| 4,541,136 A | 9/1985 | Graebe |
| 4,542,547 A * | 9/1985 | Sato .................. 5/713 |
| 4,554,930 A | 11/1985 | Kress |
| 4,573,456 A | 3/1986 | Spann |
| 4,577,185 A | 3/1986 | Andersen |
| 4,583,084 A | 4/1986 | Henderson et al. |
| 4,598,701 A | 7/1986 | Schaefer |
| 4,603,445 A | 8/1986 | Spann |
| 4,605,582 A | 8/1986 | Sias et al. |
| 4,628,556 A | 12/1986 | Blackman |
| 4,633,237 A | 12/1986 | Tucknott et al. |
| 4,637,083 A | 1/1987 | Goodwin |
| 4,638,307 A | 1/1987 | Swartout |
| 4,638,519 A | 1/1987 | Hess |
| 4,639,360 A | 1/1987 | Valyocsik |
| 4,655,505 A | 4/1987 | Kashiwamura et al. |
| 4,665,573 A | 5/1987 | Fiore |
| 4,665,574 A | 5/1987 | Filips et al. |
| 4,673,605 A | 6/1987 | Sias et al. |
| 4,679,264 A | 7/1987 | Mollura |
| 4,686,725 A | 8/1987 | Mitchell |
| 4,688,283 A | 8/1987 | Jacobson et al. |
| 4,689,844 A | 9/1987 | Alivizatos |
| 4,694,520 A | 9/1987 | Paul et al. |
| 4,694,521 A | 9/1987 | Tominaga |
| 4,698,864 A | 10/1987 | Graebe |
| 4,700,180 A | 10/1987 | Vance |
| 4,700,447 A | 10/1987 | Spann |
| 4,701,168 A | 10/1987 | Gammons |
| 4,711,275 A | 12/1987 | Ford et al. |
| 4,726,087 A | 2/1988 | Schaefer et al. |
| 4,728,551 A | 3/1988 | Jay |
| 4,730,610 A | 3/1988 | Graebe |
| 4,742,437 A | 5/1988 | Downey |
| 4,745,647 A | 5/1988 | Goodwin |
| 4,768,241 A | 9/1988 | Beney |
| 4,768,249 A | 9/1988 | Goodwin |
| 4,797,962 A * | 1/1989 | Goode .................. 5/713 |
| 4,803,625 A | 2/1989 | Fu et al. |
| 4,825,486 A | 5/1989 | Kimura et al. |
| 4,825,868 A | 5/1989 | Susa et al. |
| 4,827,763 A | 5/1989 | Bourland et al. |
| 4,829,615 A | 5/1989 | Raymond |
| 4,832,007 A | 5/1989 | Davis, Jr. et al. |
| 4,833,457 A | 5/1989 | Graebe, Jr. |
| 4,837,877 A | 6/1989 | Hamada et al. |
| 4,839,512 A | 6/1989 | Speck |
| 4,839,932 A | 6/1989 | Williamson |
| 4,845,323 A | 7/1989 | Beggs |
| 4,860,397 A | 8/1989 | Gusakov |
| 4,862,538 A | 9/1989 | Spann et al. |
| 4,884,304 A | 12/1989 | Elkins |
| 4,901,387 A | 2/1990 | Luke |
| 4,905,266 A | 2/1990 | Kuck et al. |
| 4,907,308 A | 3/1990 | Leininger et al. |
| 4,907,845 A | 3/1990 | Wood |
| D307,687 S | 5/1990 | Raburn |
| D307,688 S | 5/1990 | Schaefer |
| D307,689 S | 5/1990 | Schaefer |
| D307,690 S | 5/1990 | Raburn |
| 4,934,002 A | 6/1990 | Watanabe |
| 4,934,468 A | 6/1990 | Koerber, Sr. et al. |
| 4,944,060 A | 7/1990 | Perry et al. |
| 4,945,588 A | 8/1990 | Cassidy et al. |
| 4,947,152 A | 8/1990 | Hodges |
| 4,949,414 A | 8/1990 | Thomas et al. |
| 4,951,334 A | 8/1990 | Maier |
| 4,951,335 A | 8/1990 | Eady |
| 4,953,244 A | 9/1990 | Koerber, Sr. et al. |
| 4,953,913 A | 9/1990 | Graebe |
| 4,962,552 A | 10/1990 | Hasty |
| 4,969,459 A | 11/1990 | Gusakov |
| 4,982,466 A | 1/1991 | Higgins et al. |
| 4,989,283 A | 2/1991 | Krouskop |
| 4,991,244 A | 2/1991 | Walker |
| 4,993,920 A | 2/1991 | Harkleroad et al. |
| 4,995,124 A | 2/1991 | Wridge, Jr. et al. |
| 5,003,654 A | 4/1991 | Vrzalik |

| Patent No. | Date | Inventor |
|---|---|---|
| 5,005,240 A | 4/1991 | Vrzalik |
| 5,007,124 A | 4/1991 | Raburn et al. |
| 5,008,141 A | 4/1991 | Shinozuka |
| 5,010,610 A | 4/1991 | Ackley |
| 5,010,772 A | 4/1991 | Bourland et al. |
| 5,010,774 A | 4/1991 | Kikuo et al. |
| 5,014,375 A | 5/1991 | Coonrad et al. |
| 5,016,268 A | 5/1991 | Lotman |
| 5,020,176 A | 6/1991 | Dotson |
| 5,025,519 A | 6/1991 | Spann et al. |
| 5,029,352 A | 7/1991 | Hargest et al. |
| 5,036,559 A | 8/1991 | Hargest |
| 5,039,158 A | 8/1991 | Maier |
| 5,044,029 A | 9/1991 | Vrzalik |
| 5,048,137 A | 9/1991 | Rogers |
| 5,052,068 A | 10/1991 | Graebe |
| 5,060,174 A | 10/1991 | Gross |
| 5,062,169 A | 11/1991 | Kennedy et al. |
| 5,067,189 A | 11/1991 | Weedling et al. |
| 5,068,935 A | 12/1991 | Hagopian |
| 5,070,560 A | 12/1991 | Wilkinson |
| 5,072,468 A | 12/1991 | Hagopian |
| D322,907 S | 1/1992 | Raburn |
| 5,090,077 A | 2/1992 | Caden et al. |
| 5,092,415 A | 3/1992 | Asano |
| 5,103,519 A | 4/1992 | Hasty |
| 5,105,488 A | 4/1992 | Hutchinson et al. |
| 5,109,561 A | 5/1992 | Schild |
| 5,111,544 A | 5/1992 | Graebe |
| D326,976 S | 6/1992 | Wickis, Jr. et al. |
| 5,117,518 A | 6/1992 | Schild |
| 5,121,512 A | 6/1992 | Kaufmann |
| 5,129,115 A | 7/1992 | Higgins et al. |
| 5,136,741 A | 8/1992 | Balonick et al. |
| 5,137,102 A | 8/1992 | Houston, Sr. et al. |
| 5,140,309 A | 8/1992 | Gusakov |
| 5,142,717 A | 9/1992 | Everard et al. |
| 5,144,284 A | 9/1992 | Hammett |
| 5,144,705 A | 9/1992 | Rogers |
| 5,148,706 A | 9/1992 | Masuda et al. |
| 5,152,021 A | 10/1992 | Vrzalik |
| 5,152,023 A | 10/1992 | Graebe |
| 5,152,319 A | 10/1992 | Hannagan et al. |
| 5,163,196 A | 11/1992 | Graebe et al. |
| 5,168,589 A | 12/1992 | Stroh et al. |
| 5,172,439 A | 12/1992 | Farley |
| 5,179,742 A | 1/1993 | Oberle |
| 5,180,619 A | 1/1993 | Landi et al. |
| 5,181,288 A | 1/1993 | Heaton et al. |
| 5,182,826 A | 2/1993 | Thomas et al. |
| 5,183,039 A | 2/1993 | Sarian et al. |
| 5,184,112 A | 2/1993 | Gusakov |
| 5,184,122 A | 2/1993 | Decious et al. |
| 5,189,742 A | 3/1993 | Schild |
| 5,194,847 A | 3/1993 | Taylor et al. |
| 5,201,780 A | 4/1993 | Dinsmoor, III et al. |
| D336,400 S | 6/1993 | Mitchell et al. |
| 5,216,768 A | 6/1993 | Bodine et al. |
| D337,217 S | 7/1993 | Strickland |
| 5,234,065 A | 8/1993 | Schmidt |
| 5,235,319 A | 8/1993 | Hill et al. |
| 5,237,501 A | 8/1993 | Gusakov |
| 5,249,319 A | 10/1993 | Higgs |
| 5,251,347 A | 10/1993 | Hopper et al. |
| 5,251,349 A | 10/1993 | Thomas et al. |
| 5,252,278 A | 10/1993 | Spann et al. |
| 5,253,656 A | 10/1993 | Rincoe et al. |
| 5,255,404 A | 10/1993 | Dinsmoor, III et al. |
| 5,265,293 A | 11/1993 | Spahn et al. |
| D342,411 S | 12/1993 | Graebe |
| 5,267,364 A | 12/1993 | Volk |
| 5,269,030 A | 12/1993 | Pahno et al. |
| D343,531 S | 1/1994 | Hagopian |
| 5,276,432 A | 1/1994 | Travis |
| 5,281,000 A | 1/1994 | Ackley |
| 5,289,030 A | 2/1994 | Yamazaki et al. |
| 5,303,436 A | 4/1994 | Dinsmoor, III et al. |
| 5,316,041 A | 5/1994 | Ramacier, Jr. et al. |
| 5,325,551 A | 7/1994 | Tappel et al. |
| 5,331,549 A | 7/1994 | Crawford, Jr. |
| 5,350,417 A | 9/1994 | Augustine |
| 5,353,012 A | 10/1994 | Barham et al. |
| 5,362,543 A | 11/1994 | Nickerson |
| 5,364,162 A | 11/1994 | Bar et al. |
| 5,369,826 A | 12/1994 | Ikeda |
| 5,369,828 A | 12/1994 | Graebe |
| 5,373,595 A | 12/1994 | Hogan |
| 5,375,604 A | 12/1994 | Kelly et al. |
| 5,377,369 A | 1/1995 | Shirai |
| 5,377,373 A | 1/1995 | Shirai |
| 5,379,471 A | 1/1995 | Holdredge |
| D355,322 S | 2/1995 | Ackley et al. |
| D355,488 S | 2/1995 | Hargest et al. |
| 5,388,290 A | 2/1995 | Shirai |
| 5,398,354 A | 3/1995 | Balonick et al. |
| D357,740 S | 4/1995 | Kennemore |
| 5,402,542 A | 4/1995 | Viard |
| 5,408,754 A | 4/1995 | Raab |
| 5,410,297 A | 4/1995 | Joseph et al. |
| 5,412,821 A | 5/1995 | Wilkinson |
| D359,190 S | 6/1995 | Hargest et al. |
| 5,430,901 A | 7/1995 | Farley |
| 5,441,047 A | 8/1995 | David et al. |
| 5,444,881 A | 8/1995 | Landi et al. |
| D362,578 S | 9/1995 | Ackley |
| 5,448,788 A | 9/1995 | Wu |
| 5,448,789 A | 9/1995 | Shirai |
| 5,448,996 A | 9/1995 | Bellin et al. |
| 5,452,940 A | 9/1995 | Maier |
| 5,461,741 A | 10/1995 | Graebe |
| 5,469,591 A | 11/1995 | Nomura |
| 5,471,198 A | 11/1995 | Newham |
| 5,482,050 A | 1/1996 | Smokoff et al. |
| 5,483,709 A | 1/1996 | Foster et al. |
| 5,483,711 A | 1/1996 | Hargest et al. |
| 5,487,196 A | 1/1996 | Wilkinson et al. |
| 5,494,046 A | 2/1996 | Cross |
| 5,494,051 A | 2/1996 | Schneider, Sr. |
| 5,500,965 A | 3/1996 | Hannagan et al. |
| 5,509,155 A | 4/1996 | Zigarac et al. |
| 5,511,260 A | 4/1996 | Dinsmoor, III et al. |
| D370,066 S | 5/1996 | Kennemore |
| 5,534,851 A | 7/1996 | Russek |
| 5,539,942 A | 7/1996 | Melou |
| 5,539,943 A | 7/1996 | Romano |
| 5,542,136 A | 8/1996 | Tappel |
| 5,542,138 A | 8/1996 | Williams et al. |
| 5,544,649 A | 8/1996 | David et al. |
| 5,554,835 A | 9/1996 | Newham |
| 5,555,224 A | 9/1996 | DePonty et al. |
| 5,555,578 A | 9/1996 | Wyatt et al. |
| 5,558,638 A | 9/1996 | Evers et al. |
| D374,368 S | 10/1996 | Sprigle et al. |
| 5,560,374 A | 10/1996 | Viard |
| 5,561,873 A | 10/1996 | Weedling |
| 5,561,875 A | 10/1996 | Graebe |
| 5,564,142 A | 10/1996 | Liu |
| 5,580,504 A | 12/1996 | Spann et al. |
| 5,583,832 A | 12/1996 | DePonty |
| 5,586,346 A | 12/1996 | Stacy et al. |
| 5,588,167 A | 12/1996 | Pshno et al. |
| 5,596,781 A | 1/1997 | Graebe |
| 5,611,094 A | 3/1997 | D'Entremont |
| 5,611,096 A | 3/1997 | Bartlett et al. |
| 5,611,772 A | 3/1997 | Fujimoto et al. |
| 5,623,736 A | 4/1997 | Soltani et al. |

| | | | | | | |
|---|---|---|---|---|---|---|
| 5,630,238 A | 5/1997 | Weismiller et al. | D415,834 S | 10/1999 | Bar | |
| 5,633,627 A | 5/1997 | Newham | 5,963,137 A | 10/1999 | Waters, Sr. | |
| 5,634,224 A | 6/1997 | Gates | 5,966,762 A * | 10/1999 | Wu | 5/710 |
| 5,634,225 A | 6/1997 | Miller, Sr. et al. | 5,966,763 A | 10/1999 | Thomas et al. | |
| 5,649,331 A | 7/1997 | Wilkinson et al. | 5,970,550 A | 10/1999 | Gazes | |
| 5,651,151 A | 7/1997 | Schild | 5,970,789 A | 10/1999 | Meyer et al. | |
| 5,652,985 A | 8/1997 | Wilkinson et al. | D416,326 S | 11/1999 | Bar | |
| 5,654,694 A | 8/1997 | Newham | 5,983,428 A | 11/1999 | Hannagan | |
| 5,664,270 A | 9/1997 | Bell et al. | 5,983,429 A | 11/1999 | Stacy et al. | |
| 5,666,681 A | 9/1997 | Meyer et al. | 5,984,418 A | 11/1999 | McInturff | |
| D386,035 S | 11/1997 | Matsler et al. | 5,987,668 A | 11/1999 | Ackley | |
| 5,687,438 A | 11/1997 | Biggie et al. | 5,989,285 A | 11/1999 | De Vilbiss et al. | |
| 5,689,845 A | 11/1997 | Sobieralski | 5,990,799 A | 11/1999 | Boon et al. | |
| 5,692,256 A * | 12/1997 | Kramer et al. ................. 5/624 | 5,991,949 A * | 11/1999 | Miller et al. | 5/710 |
| 5,699,570 A | 12/1997 | Wilkinson et al. | 5,993,400 A | 11/1999 | Rincoe et al. | |
| 5,701,622 A | 12/1997 | Biggie et al. | 5,994,450 A | 11/1999 | Pearce | |
| D388,995 S | 1/1998 | Hargest et al. | 6,006,383 A | 12/1999 | Pile et al. | |
| D390,404 S | 2/1998 | Hargest et al. | 6,007,898 A | 12/1999 | Kim et al. | |
| D390,665 S | 2/1998 | Kennemore | 6,009,580 A | 1/2000 | Caminade et al. | |
| 5,715,548 A | 2/1998 | Weismiller et al. | 6,014,346 A | 1/2000 | Malone | |
| D393,071 S | 3/1998 | Kennemore | 6,025,782 A | 2/2000 | Newham | |
| 5,731,062 A * | 3/1998 | Kim et al. ................... 428/175 | 6,026,527 A | 2/2000 | Pearce | |
| 5,737,788 A | 4/1998 | Castellino et al. | 6,030,351 A | 2/2000 | Schmidt et al. | |
| D394,578 S | 5/1998 | Raburn | 6,036,271 A | 3/2000 | Wilkinson et al. | |
| 5,745,939 A | 5/1998 | Flick et al. | 6,036,660 A | 3/2000 | Toms | |
| 5,749,111 A | 5/1998 | Pearce | 6,047,424 A | 4/2000 | Osborne et al. | |
| 5,749,374 A | 5/1998 | Schneider, Sr. | 6,049,281 A | 4/2000 | Osterweil | |
| 5,755,000 A | 5/1998 | Thompson | 6,049,927 A | 4/2000 | Thomas et al. | |
| 5,765,564 A | 6/1998 | Ewing | 6,058,537 A | 5/2000 | Larson | |
| 5,767,774 A | 6/1998 | Wright et al. | 6,058,538 A | 5/2000 | Chapman et al. | |
| 5,771,511 A | 6/1998 | Kummer et al. | 6,067,019 A | 5/2000 | Scott | |
| 5,780,798 A | 7/1998 | Hall-Jackson | 6,073,289 A | 6/2000 | Bolden et al. | |
| 5,781,949 A | 7/1998 | Weismiller et al. | 6,076,208 A | 6/2000 | Heimbrock et al. | |
| 5,785,716 A | 7/1998 | Bayron et al. | 6,078,253 A | 6/2000 | Fowler | |
| D397,443 S | 8/1998 | Fletcher et al. | 6,078,261 A | 6/2000 | Davsko | |
| 5,787,528 A | 8/1998 | Antinori | 6,079,070 A | 6/2000 | Flick | |
| 5,787,531 A | 8/1998 | Pepe | 6,085,372 A | 7/2000 | James et al. | |
| 5,794,288 A | 8/1998 | Soltani et al. | 6,094,762 A | 8/2000 | Viard et al. | |
| 5,794,289 A | 8/1998 | Wortman et al. | 6,095,611 A | 8/2000 | Bar et al. | |
| 5,796,059 A | 8/1998 | Boon | 6,111,509 A | 8/2000 | Holmes | |
| 5,797,155 A | 8/1998 | Maier et al. | 6,115,860 A | 9/2000 | Vrzalik | |
| 5,808,552 A | 9/1998 | Wiley et al. | 6,129,686 A | 10/2000 | Friedman | |
| 5,815,862 A | 10/1998 | Rygiel | 6,131,469 A | 10/2000 | Wortman et al. | |
| 5,815,864 A * | 10/1998 | Sloop ............................ 5/706 | 6,133,837 A | 10/2000 | Riley | |
| 5,815,865 A | 10/1998 | Washburn et al. | 6,134,732 A | 10/2000 | Chapman et al. | |
| 5,829,081 A | 11/1998 | Pearce | 6,138,302 A | 10/2000 | Sashin et al. | |
| 5,838,244 A | 11/1998 | Schmidt et al. | 6,140,921 A | 10/2000 | Baron et al. | |
| 5,840,400 A | 11/1998 | Landi et al. | 6,145,142 A * | 11/2000 | Rechin et al. | 5/706 |
| 5,844,488 A | 12/1998 | Musick | 6,145,143 A | 11/2000 | Hicks et al. | |
| 5,845,352 A | 12/1998 | Matsler et al. | 6,146,332 A | 11/2000 | Pinsonneault et al. | |
| 5,848,450 A | 12/1998 | Oexman et al. | 6,148,461 A | 11/2000 | Cook et al. | |
| D403,773 S | 1/1999 | Fletcher et al. | 6,154,907 A * | 12/2000 | Cinquin | 5/713 |
| 5,869,164 A | 2/1999 | Nickerson et al. | 6,165,142 A | 12/2000 | Bar | |
| 5,873,137 A | 2/1999 | Yavets-Chen | 6,166,644 A | 12/2000 | Stroda | |
| D407,353 S | 3/1999 | Bar et al. | 6,175,752 B1 | 1/2001 | Say et al. | |
| 5,879,309 A | 3/1999 | Johnson et al. | 6,182,316 B1 | 2/2001 | Thomas et al. | |
| 5,882,349 A | 3/1999 | Wilkerson et al. | D439,098 S | 3/2001 | Matsler et al. | |
| D408,767 S | 4/1999 | Bar et al. | 6,202,237 B1 | 3/2001 | Chang | |
| 5,901,391 A | 5/1999 | Kato | 6,204,767 B1 | 3/2001 | Sparks | |
| 5,901,393 A | 5/1999 | Pepe et al. | 6,208,250 B1 | 3/2001 | Dixon et al. | |
| D411,301 S | 6/1999 | Hampson et al. | 6,212,718 B1 | 4/2001 | Stolpmann et al. | |
| 5,913,774 A | 6/1999 | Feddema | 6,216,300 B1 | 4/2001 | Hannagan | |
| 5,917,180 A | 6/1999 | Reimer et al. | 6,223,369 B1 | 5/2001 | Maier et al. | |
| 5,926,883 A | 7/1999 | Rechin et al. | 6,230,342 B1 | 5/2001 | Haugs | |
| 5,926,884 A | 7/1999 | Biggie et al. | 6,239,704 B1 | 5/2001 | Olson | |
| D412,685 S | 8/1999 | Bar et al. | 6,240,584 B1 | 6/2001 | Perez et al. | |
| D413,085 S | 8/1999 | Bar et al. | 6,255,956 B1 | 7/2001 | Tingley et al. | |
| 5,934,280 A | 8/1999 | Viard et al. | 6,256,819 B1 | 7/2001 | Maier et al. | |
| 5,941,836 A | 8/1999 | Friedman | 6,256,822 B1 | 7/2001 | Weston et al. | |
| D413,841 S | 9/1999 | Bar et al. | 6,260,221 B1 | 7/2001 | Grabell et al. | |
| 5,954,402 A | 9/1999 | McInturff | D446,674 S | 8/2001 | Chapman et al. | |
| 5,957,872 A | 9/1999 | Flick | 6,269,505 B1 | 8/2001 | Wilkinson | |
| D415,567 S | 10/1999 | Bar | 6,271,760 B1 | 8/2001 | Watanabe et al. | |

| | | | | | | |
|---|---|---|---|---|---|---|
| 6,272,707 B1 * | 8/2001 | Robrecht et al. ............... 5/724 | | 6,725,479 B1 | 4/2004 | Stryker et al. |
| 6,279,183 B1 | 8/2001 | Kummer et al. | | 6,727,445 B2 | 4/2004 | Cullinan et al. |
| 6,280,392 B1 | 8/2001 | Yoshimi et al. | | 6,730,115 B1 | 5/2004 | Heaton |
| 6,287,253 B1 | 9/2001 | Ortega et al. | | 6,735,799 B1 | 5/2004 | Ellis et al. |
| 6,295,675 B1 * | 10/2001 | Ellis et al. ...................... 5/710 | | 6,735,801 B2 | 5/2004 | Henley et al. |
| 6,297,738 B1 | 10/2001 | Newham | | 6,760,939 B2 | 7/2004 | Ellis et al. |
| 6,307,476 B1 | 10/2001 | Smith et al. | | 6,782,574 B2 | 8/2004 | Totton et al. |
| 6,315,740 B1 | 11/2001 | Singh | | 6,848,135 B1 * | 2/2005 | Kohlman ...................... 5/654 |
| 6,317,912 B1 | 11/2001 | Graebe et al. | | 6,877,178 B2 | 4/2005 | Chapman et al. |
| 6,320,510 B2 | 11/2001 | Menkedick et al. | | 2001/0001235 A1 | 5/2001 | Menkedick et al. |
| 6,349,439 B1 | 2/2002 | Cook et al. | | 2001/0011480 A1 | 8/2001 | Reimer |
| 6,351,863 B1 | 3/2002 | Meyer et al. | | 2001/0023511 A1 | 9/2001 | Wilkinson |
| 6,353,394 B1 | 3/2002 | Maeda et al. | | 2001/0029628 A1 | 10/2001 | Ferrand et al. |
| 6,353,950 B1 | 3/2002 | Bartlett et al. | | 2002/0066143 A1 | 6/2002 | Graebe et al. |
| 6,357,065 B1 | 3/2002 | Adams | | 2002/0067273 A1 | 6/2002 | Jaques et al. |
| 6,357,066 B1 | 3/2002 | Pierce | | 2002/0070867 A1 | 6/2002 | Conway et al. |
| 6,357,491 B1 | 3/2002 | Buchanan et al. | | 2002/0073489 A1 | 6/2002 | Totton et al. |
| 6,370,716 B1 | 4/2002 | Wilkinson | | 2002/0080037 A1 | 6/2002 | Dixon et al. |
| 6,375,633 B1 | 4/2002 | Endress et al. | | 2002/0128572 A1 | 9/2002 | Chang |
| 6,378,152 B1 | 4/2002 | Washburn et al. | | 2002/0138910 A1 | 10/2002 | Boyd |
| 6,384,728 B1 | 5/2002 | Kanor et al. | | 2002/0148046 A1 | 10/2002 | Pirzada |
| 6,385,804 B1 | 5/2002 | Barber et al. | | 2002/0186136 A1 | 12/2002 | Schuman |
| 6,393,642 B1 | 5/2002 | Pollman et al. | | 2002/0196148 A1 | 12/2002 | Nunome |
| 6,401,283 B2 | 6/2002 | Thomas et al. | | 2003/0014817 A1 | 1/2003 | Gallant et al. |
| 6,403,196 B1 | 6/2002 | Bessey et al. | | 2003/0024051 A2 | 2/2003 | Wilkinson |
| 6,417,777 B2 | 7/2002 | Fitzgerald et al. | | 2003/0026971 A1 | 2/2003 | Inkster et al. |
| 6,421,859 B1 | 7/2002 | Hicks et al. | | 2003/0030319 A1 | 2/2003 | Clapper |
| 6,438,776 B2 | 8/2002 | Ferrand et al. | | 2003/0063010 A1 | 4/2003 | Smith et al. |
| 6,441,742 B1 | 8/2002 | Lovely et al. | | 2003/0073936 A1 | 4/2003 | Raisanen |
| 6,442,780 B1 | 9/2002 | Phillips et al. | | 2003/0079549 A1 | 5/2003 | Lokhorst et al. |
| D463,701 S | 10/2002 | Borcherding et al. | | 2003/0090383 A1 | 5/2003 | Conway |
| 6,467,111 B1 | 10/2002 | Vrzalik et al. | | 2003/0114736 A1 | 6/2003 | Reed et al. |
| 6,468,234 B1 | 10/2002 | Van der Loos et al. | | 2003/0145386 A1 | 8/2003 | Kemp |
| 6,474,743 B1 | 11/2002 | Harker et al. | | 2003/0182728 A1 | 10/2003 | Chapman et al. |
| 6,485,441 B2 | 11/2002 | Woodward | | 2003/0208849 A1 | 11/2003 | Wilkinson |
| 6,487,739 B1 | 12/2002 | Harker | | 2003/0216670 A1 | 11/2003 | Beggs |
| 6,493,568 B1 | 12/2002 | Bell et al. | | 2003/0236474 A1 | 12/2003 | Singh |
| 6,499,167 B1 | 12/2002 | Ellis et al. | | 2004/0015103 A1 | 1/2004 | Aminian et al. |
| 6,517,510 B1 | 2/2003 | Stewart et al. | | 2004/0046668 A1 | 3/2004 | Smith et al. |
| 6,544,200 B1 | 4/2003 | Smith et al. | | 2004/0064072 A1 | 4/2004 | Shapira |
| 6,550,085 B2 | 4/2003 | Roux | | 2007/0163052 A1 | 7/2007 | Romano et al. |
| 6,556,149 B1 | 4/2003 | Reimer et al. | | | | |
| 6,560,803 B2 | 5/2003 | Zur | | | | |
| 6,560,804 B2 | 5/2003 | Wise et al. | | FOREIGN PATENT DOCUMENTS | | |
| 6,564,404 B1 | 5/2003 | Nanahara | | | | |
| 6,564,405 B1 | 5/2003 | Barr et al. | | DE | 29502025 | 6/1996 |
| 6,564,410 B2 | 5/2003 | Graebe et al. | | DE | 10318162 A1 | 10/2004 |
| 6,564,411 B2 | 5/2003 | Pirzada | | DE | 10333742 A1 | 2/2005 |
| 6,566,833 B2 | 5/2003 | Bartlett | | EP | 218301 A2 | 4/1987 |
| 6,568,273 B2 | 5/2003 | Reimer | | EP | 218301 A3 | 7/1988 |
| 6,582,456 B1 | 5/2003 | Hand et al. | | EP | 663169 B1 | 7/1995 |
| 6,578,219 B1 | 6/2003 | Gabel et al. | | EP | 853 918 A2 | 7/1998 |
| 6,583,727 B2 | 6/2003 | Nunome | | EP | 0908168 B1 | 4/1999 |
| 6,591,437 B1 | 7/2003 | Phillips | | FR | 2 596 950 | 10/1987 |
| 6,593,588 B1 | 7/2003 | Reimer | | FR | 2814062 | 3/2002 |
| 6,606,754 B1 | 8/2003 | Flick | | GB | 159299 | 2/1921 |
| 6,611,783 B2 | 8/2003 | Kelly, Jr. et al. | | GB | 2235776 A | 3/1991 |
| 6,623,080 B2 | 9/2003 | Clapper | | GB | 2329250 A | 3/1999 |
| 6,646,556 B1 | 11/2003 | Smith et al. | | JP | 2007-159981 | 6/2007 |
| 6,662,391 B2 | 12/2003 | Wilson et al. | | WO | WO94/09686 | 5/1994 |
| 6,668,399 B2 | 12/2003 | Malstaff et al. | | WO | WO96/33641 | 10/1996 |
| 6,671,905 B2 | 1/2004 | Bartlett et al. | | WO | WO 98/20828 A1 | 5/1998 |
| 6,684,430 B2 | 2/2004 | Roux | | WO | WO 99/11204 A1 | 3/1999 |
| 6,687,936 B2 | 2/2004 | Graebe et al. | | WO | WO 00/03625 A2 | 1/2000 |
| 6,687,937 B2 | 2/2004 | Harker | | WO | WO 00/51541 A3 | 9/2000 |
| 6,687,987 B2 | 2/2004 | Harker | | WO | WO 03/005935 A3 | 1/2003 |
| 6,689,079 B2 | 2/2004 | Flick et al. | | WO | WO 03/006074 A3 | 1/2003 |
| 6,691,345 B2 | 2/2004 | Nanahara | | WO | WO 03/041538 A1 | 5/2003 |
| 6,701,556 B2 | 3/2004 | Romano et al. | | WO | WO 03/073825 A2 | 9/2003 |
| 6,715,169 B2 | 4/2004 | Niederkrom | | WO | WO03073825 A3 | 9/2003 |
| 6,719,708 B1 | 4/2004 | Jansen | | WO | WO 2004/006768 A1 | 1/2004 |
| 6,721,979 B2 | 4/2004 | Vrzalik et al. | | | | |
| 6,721,980 B1 | 4/2004 | Price et al. | | | | |

| | | | |
|---|---|---|---|
| WO | WO2005/013878 | 2/2005 | |

OTHER PUBLICATIONS

Hill-Rom, PrimeAire® ARS Pressure Relief Mattress, Hill-Rom Company, Inc., Batesville, Indiana, 2004, 4 pgs.
Cushions, Wheelchair, Crown Therapeutics, Inc., Feb. 10, 2004, 1 pg.
Roho® High Profile Specs, Features and benefits of the Roho® High Profile Cushion, the ROHO group, See www.woundheal.com/products/rohoProd03.htm, Date Feb. 10, 2004, 2 pgs.
Roho® High Profile Specs, Features and benefits of the Roho® High Profile Dual Compartment Cushion, the ROHO group, See www.woundheal.com/products/rohoProd04.htm, Date Feb. 10, 2004, 2 pgs.
Roho® Low Profile Specs, Features and benefits of the Roho® Low Profile Therapeutic Cushion, the ROHO group, See www.woundheal.com/products/rohoProd05.htm, Date: Feb. 10, 2004, 2 pgs.
Roho® Dual Compartment Therapeutic Cushion Specs, Features and benefits of the Roho® Low Profile Dual Compartment therapeutic cushion, the ROHO group, See www.woundheal.com/products/rohoProd06.htm, Date: Feb. 10, 2004, 2 pgs.
Roho® Dry Floatation Specs, Features and Benefits of the Roho® Dry Floatation Mattress, the ROHO® group, See www.woundheal.com/products/rohoProd01/htm, Date Feb. 10, 2004, 1 pg.
Roho® Dry Floatation® Mattress, the ROHO group, See www.roho.com/medical/dryfloat.jsp, Date Mar. 18, 2004, 1 pg.
SOFFLEX® Mattress Overlay, the ROHO® group, See www.roho.com/medical/sofflex.jsp, Date Mar. 18, 2004, 1 pg.
Crown Pressure Support Systems, Crown Therapeutics Inc.®, See www.carecatalogservices/manufacturer/crown_press_supp_sys.htm, , Date Feb. 10, 2004, 6 pgs.
Crown Therapeutics—Prodigy Mattress Overlay, Crown Therapeutics Inc.®, See www.shop.store.yahoo.com/medicalsupplydepo/crthprmaov.html Date Feb. 10, 2004, 1 pg.
Office Action mailed from the United States Patent and Trademark Office on May 21, 2007 for U.S. Appl. No. 11/324,447 (21 pages).
GAYMAR Soft-Care Plus® Companion System, Gaymar Industries, Inc., 1994.
First Step, Mattress Replacement System, KCI, San Antonio, TX, 1991.
Impression, Pressure Relief Therapy, KCI.
LUMEX Akro Tech 4000, Lumex.
MicroAIRO 1000, GSI Medical Systems, Carmel, NY 1989.
Pro 2000 MRS, Pneu-Care Series, Cardio Systems, Dallas, TX.
Prodigy Mattress Crown Theraputics, Inc.
Roho Dry Flotation Isolette see roho.com/medical/isolette.jsp.
ROHO series Crown Theraputic, Inc., See woundheal.com.
Tytex Group AirX #D Spacer Fabric see tytex.cmc.digitalis.dk.
Renaissance™ Therapeutic Mattress Replacement System, Pegasus Airwave Inc.
Air Flow 5000 Mattress Replacement System, Atlantis Medical, Milltown, NJ.
Apropros, CRS-8500, National Patient Care Systems.
ASAP II Therapy System, DynaMedics Corporation, London, ON, Canada Mar. 1995.
Bazooka, Innovative Medical Systems, Manchester, NH, 1995.
DFS® Homecare Advanced Dynamic Flotation System, HNE Healthcare, Manalapan, NJ.
Economic Relief, Bio Therapy ® Plus, Sunrise Medical Bio Clinic, Ontario, CA.
Office Action mailed from the United States Patent and Trademark Office on Nov. 26, 2007 for U.S. Appl. No. 11/324,447 (9 pages).

* cited by examiner

PATIENT SUPPORT

CROSS-REFERENCE TO RELATED APPLICATIONS

This application is a continuation of U.S. patent application Ser. No. 11/120,080 to Bobey et al, entitled PATIENT SUPPORT, filed May 2, 2005, which claims the benefit of U.S. Provisional Patent Application Ser. No. 60/567,215 to Balaton et al., entitled PRESSURE RELIEF SUPPORT SURFACE, filed Apr. 30, 2004, and U.S. Provisional Patent Application Ser. No. 60/665,241 of Hopkins et al., entitled THERMOREGULATING DEVICE WITH SUPPORT CELLS, filed Mar. 25, 2005, and U.S. Provisional Patent Application Ser. No. 60/665,141 of Hopkins et al., entitled THERMOREGULATING DEVICE, filed Mar. 25, 2005, and U.S. Provisional Patent Application Ser. No. 60/636,252 of Chambers et al., entitled QUICK CONNECTOR FOR MULTIMEDIA, filed Dec. 15, 2004, and U.S. Provisional Patent Application Ser. No. 60/608,013 of Branson, entitled ROTATION SENSOR FOR A MATTRESS, filed Sep. 8, 2004, and all of which are incorporated herein by this reference in their entirety. The inventors of the above applications and the inventors of the present invention are obligated to assign their rights to the same assignee.

The present application is also related to U.S. patent application Ser. No. 11/119,980, entitled PRESSURE RELIEF SURFACE, and U.S. patent application Ser. No. 11/119,991, entitled PATIENT SUPPORT HAVING REAL TIME PRESSURE CONTROL, and U.S. patent application Ser. No. 11/119,635, entitle LACK OF PATIENT MOVEMENT MONITOR AND METHOD, all of which are filed on the same date herewith, and all of which are incorporated herein by this reference. The inventors of the above applications and the inventors of the present invention are obligated to assign their rights to the same assignee.

In addition, PCT patent application, entitled BODY SUPPORT APPARATUS HAVING AUTOMATIC PRESSURE CONTROL AND RELATED METHODS of Lokhorst et al. PCT CA05/00658, WO 2005 104904 of Oyen, Wiggs, Green & Mutala LLP, Vancouver, BC, Canada) filed on the same date herewith is incorporated herein by this reference in its entirety.

BACKGROUND OF THE DISCLOSURE

The present disclosure relates to a device for supporting a patient, such as a mattress. In particular, the present disclosure relates to patient supports appropriate for use in hospitals, acute care facilities, and other patient care environments. Certain embodiments disclosed herein relate to pressure relief support surfaces, or patient support surfaces that are configured to accommodate and operate with a variety of sizes and styles of beds, bed frames, and patient types.

SUMMARY OF THE DISCLOSURE

In one illustrated embodiment of the present invention, a patient support is provided that has a cover defining an interior region. A base is positioned in the interior region. Inflatable bladders extend upwardly from the base along a vertical axis. The vertical axis is substantially perpendicular to the base.

Pressure sensors may be positioned underneath the base. The pressure sensors may be arranged so that each sensor is aligned with at least one of the vertical bladders. The pressure sensors may be enclosed within an enclosure. The enclosure may be located in the interior region of the cover.

The pressure sensors may include one or more light transmitters or conductors or optical fibers. The pressure sensors may operate to measure pressure applied to one or more of the bladders. One or more of the pressure sensors may evaluate changes in intensity of light energy diffused within the sensor.

One or more pressure transducers may be coupled to the inflatable bladders. The pressure transducers may operate to measure internal pressure of fluid within the bladders.

A support layer may be positioned above the inflatable bladders. The support layer may have at least one support characteristic that is different from a support characteristic of the inflatable bladders. The support layer may include a breathable or air-permeable material. The support layer may include resilient portions. The support layer may include projections and depressions. The support layer may be enclosed within an enclosure. The enclosure may be located in the interior region of the cover.

The inflatable bladders may be substantially can-shaped or cylindrical. One or more of the inflatable bladders may include a beveled portion located between a top portion and a vertical portion of the bladder.

The patient support may include one or more removable filler portions. The filler portions may be selected to conform the patient support to bed frames having one or more deck configurations, including flat deck and step or recessed deck configurations.

BRIEF DESCRIPTION OF THE DRAWINGS

Aspects of the present invention are more particularly described below with reference to the following figures, which illustrate exemplary embodiments of the present invention.

DETAILED DESCRIPTION OF ILLUSTRATED EMBODIMENTS

Figure 1:
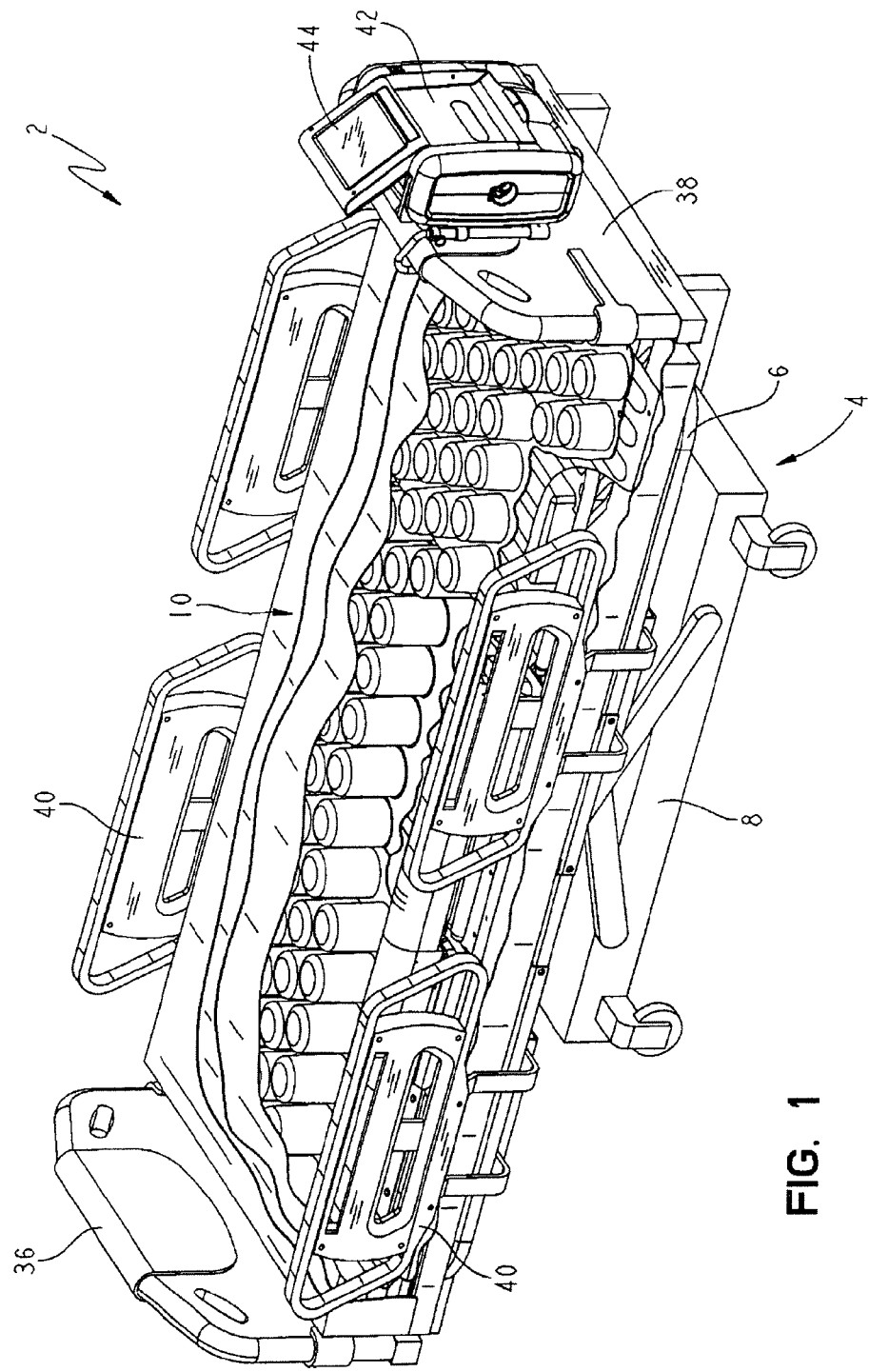
FIG. 1 is a perspective view of a patient support positioned on an exemplary hospital bed, with a portion of the patient support being cut away to show interior components of the patient support.

FIG. 1 shows an embodiment of a patient support or mattress 10 in accordance with the present invention. Patient support 10 is positioned on an exemplary bed 2. Bed 2, as illustrated, is a hospital bed including a frame 4, a headboard 36, a footboard 38, and a plurality of siderails 40.

Frame 4 of the exemplary bed 2 generally includes a deck 6 supported by a base 8. Deck 6 includes one or more deck sections (not shown), some or all of which may be articulating sections, i.e., pivotable with respect to base 8. In general, patient support 10 is configured to be supported by deck 6.

Patient support 10 has an associated control unit 42, which controls inflation and deflation of certain internal components of patient support 10, among other things. Control unit 42 includes a user interface 44, which enables caregivers, service technicians, and/or service providers to configure patient support 10 according to the needs of a particular patient. For example, support characteristics of patient support 10 may be adjusted according to the size, weight, position, or activity level of the patient. User interface 44 is password-protected or otherwise designed to prevent access by unauthorized persons.

User interface 44 also enables patient support 10 to be adapted to different bed configurations. For example, deck 6 may be a flat deck or a step or recessed deck. A caregiver may select the appropriate deck configuration via user interface 44. Inflation or deflation of specific mattress components may occur in response to user selection of a hospital bed frame or deck configuration.

Figure 2:
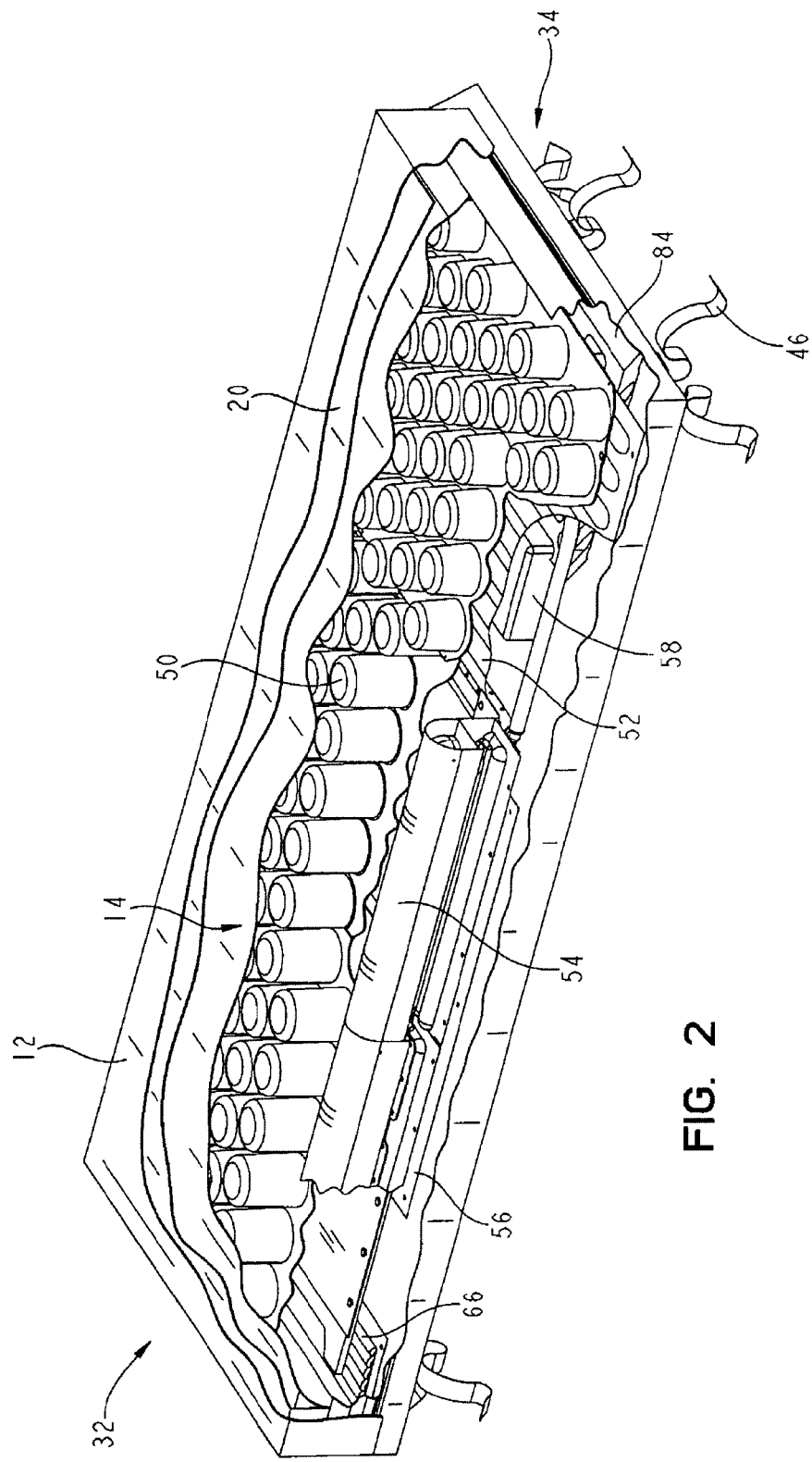
FIG. 2 is a perspective view of a patient support, with a portion being cut away to show interior components of the patient support.

Referring now to FIG. 2, patient support 10 has a head end 32 generally configured to support a patient's head and/or upper body region, and a foot end 34 generally configured to support a patient's feet and/or lower body region. Patient support 10 includes a cover 12 which defines an interior region 14. In the illustrated embodiment, interior region 14 includes a first layer 20, a second layer 50, and a third layer 52. However, it will be understood by those skilled in the art that other embodiments of the present invention may not include all three of these layers, or may include additional layers, without departing from the scope of the present invention.

In the illustrated embodiment, first layer 20 includes a support material, second layer 50 includes a plurality of vertically-oriented inflatable bladders located underneath the first layer 20, and third layer 52 includes a plurality of pressure sensors located underneath the vertical bladders of second layer 50, as more particularly described below.

Also located within interior region 14 are a plurality of bolsters 54, one or more filler portions 56, and a pneumatic valve control box 58. A fire-resistant material (not shown) may also be included in the interior region 14.

Patient support 10 may be coupled to deck 6 by one or more couplers 46. Illustratively, couplers 46 are conventional woven or knit or fabric straps including a D-ring or hook and loop assembly or Velcro®-brand strip or similar fastener. It will be understood by those skilled in the art that other suitable couplers, such as buttons, snaps, or tethers may also be used equally as well.

Figure 3:
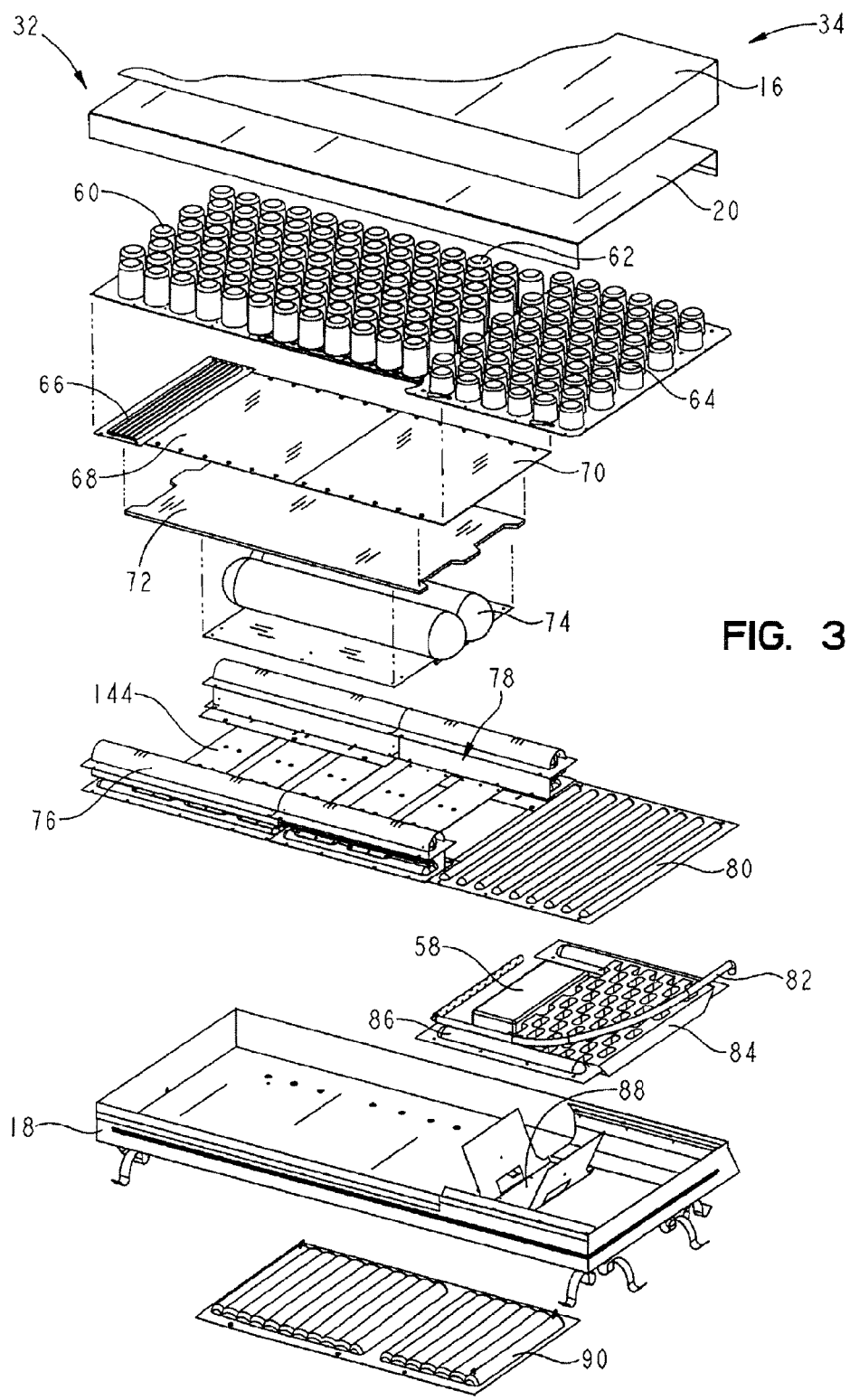
FIG. 3 is an exploded view of components of the illustrated embodiment of a patient support.

Components of one embodiment of a patient support in accordance with the present invention are shown in exploded view in FIG. 3. This embodiment of patient support 10 includes a top cover portion 16 and a bottom cover portion 18. Top cover portion 16 and bottom cover portion 18 couple together by conventional means (such as zipper, Velcro® strips, snaps, buttons, or other suitable fastener) to form cover 12, which defines interior region 14. While a plurality of layers and/or components are illustrated within interior region 14, it will be understood by those of skill in the art that the present invention does not necessarily require all of the illustrated components to be present.

Figure 4:
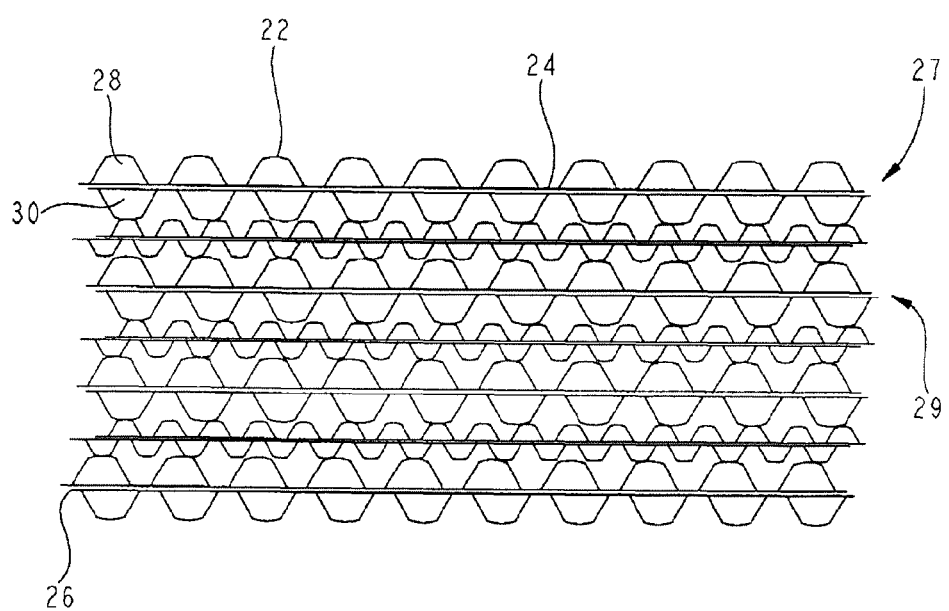
FIG. 4 is a schematic view of an exemplary three-dimensional support material.

A first support layer 20 is located below top cover portion 16 in interior region 14. First support layer 20 includes one or more materials, structures, or fabrics suitable for supporting a patient, such as foam, inflatable bladders, or three-dimensional material. Suitable three-dimensional materials include Spacenet, Tytex, and/or similar materials. One embodiment of a suitable three dimensional material for support layer 20 is shown in FIG. 4, described below.

Returning to FIG. 3, a second support layer 50 including one or more inflatable bladder assemblies, is located underneath the first support layer 20. The illustrated embodiment of the second support layer 50 includes first, second and third bladder assemblies, namely, a head section bladder assembly 60, a seat section bladder assembly 62, and a foot section bladder assembly 64. However, it will be understood by those skilled in the art that other embodiments include only one bladder assembly extending from head end 32 to foot end 34, or other arrangements of multiple bladder assemblies, for example, including an additional thigh section bladder assembly. The illustrated bladder assemblies 60, 62, 64 and their components are described below with reference to FIGS. 5-19. In general, bladder assemblies disclosed herein are formed from a lightweight, flexible air-impermeable material such as a polymeric material like polyurethane, urethane-coated fabric, vinyl, or rubber.

A pressure-sensing layer 69 illustratively including first and second sensor pads, namely a head sensor pad 68 and a seat sensor pad 70, is positioned underneath bladder assemblies 60, 62, 64. Head sensor pad 68 is generally aligned underneath head section bladder assembly 60, and seat sensor pad 70 is generally aligned underneath seat section bladder assembly 62, as shown. Head filler 66 may be positioned adjacent head sensor pad 68 near head end 32 so as to properly position head sensor pad 68 underneath the region of patient support 10 most likely to support the head or upper body section of the patient. In other embodiments, a single sensor pad or additional sensor pads, for example, located underneath foot section bladder assembly 64, and/or different alignments of the sensor pads, are provided. Sensor pads 68, 70 are described below with reference to FIGS. 20-21.

In the illustrated embodiment, a turn-assist cushion or turning bladder or rotational bladder 74 is located below sensor pads 68, 70. The exemplary turn-assist cushion 74 shown in FIG. 3 includes a pair of inflatable bladders 74a, 74b. Another suitable rotational bladder 74 is a bellows-shaped bladder. Another suitable turn-assist cushion is disclosed in, for example, U.S. Pat. No. 6,499,167 to Ellis, et al., which patent is owned by the assignee of the present invention and incorporated herein by this reference. Turn-assist cushions 74 are not necessarily a required element of the present invention.

A plurality of other support components 66, 72, 76, 78, 80, 84, 86, 90 are also provided in the embodiment of FIG. 3. One or more of these support components are provided to enable patient support 10 to be used in connection with a variety of different bed frames, in particular, a variety of bed frames having different deck configurations. One or more of these support components may be selectively inflated or deflated or added to or removed from patient support 10 in order to conform patient support 10 to a particular deck configuration, such as a step or recessed deck or a flat deck.

The support components illustrated in FIG. 3 are made of foam, inflatable bladders, three-dimensional material, other suitable support material, or a combination of these. For example, as illustrated, head filler 66 includes a plurality of foam ribs extending transversely across patient support 10. Head filler 66 could also be an inflatable bladder. Filler portion 72 includes a foam layer positioned substantially underneath the sensor pads 68, 70 and extending transversely across the patient support 10. In the illustrated embodiment, filler portion 72 includes a very firm foam, such as polyethylene closed-cell foam, with a ½-inch thickness.

Head bolster assembly 76, seat bolster assembly 78, and foot section bolster assembly 86 each include longitudinally-oriented inflatable bladders spaced apart by coupler plates 144. Bolster assemblies 76, 78, 86 are described below with reference to FIG. 22.

As illustrated, first foot filler portion 80 includes a plurality of inflatable bladders extending transversely across patient support 10, and second foot filler portion 84 includes a foam member, illustratively with portions cut out to allow for retractability of the foot section or for other reasons. Deck filler portion 90 includes a plurality of transversely-extending inflatable bladders. As illustrated, deck filler portion 90 includes two bladder sections located beneath the head and seat sections of the mattress, respectively, and is located outside of cover 12. Deck filler portion 90 may include one or more bladder regions, or may be located within interior region 14, without departing from the scope of the present invention.

Also provided in the illustrated embodiment are a pneumatic valve box 58 and an air supply tube assembly 82. Receptacle 88 is sized to house pneumatic valve box 58. In the illustrated embodiment, receptacle 88 is coupled to bottom cover portion 18 by Velcro® strips. Pneumatic box 58 and tube assembly 82 are described below with reference to FIG. 6, FIG. 23, and FIGS. 25-26.

In the illustrated embodiment, support layer 20 includes a breathable or air permeable material which provides cushioning or support for a patient positioned thereon and allows for circulation of air underneath a patient. The circulated air may be at ambient temperature, or may be cooled or warmed in order to achieve desired therapeutic effects.

Also in the illustrated embodiment, support layer 20 includes or is enclosed in a low friction air permeable material (such as spandex, nylon, or similar material) enclosure that allows support layer 20 to move with movement of a patient on patient support 10, in order to reduce shear forces, for instance. In other embodiments, the enclosure is made of a non-air permeable, moisture/vapor permeable material such as Teflon or urethane-coated fabric.

In FIG. 4, an exemplary three-dimensional material suitable for use in support layer 20 is depicted. This illustrated embodiment of support layer 20 includes a plurality of alternating first and second layers 27, 29. Each layer 27, 29 includes first and second sublayers 28, 30. As shown, the sublayers 28, 30 are positioned back-to-back and each sublayer 28, 30 includes a plurality of peaks or semicircular, cone, or dome-shaped projections 22 and troughs or depressions 24. A separator material 26 is provided between the first and second sublayers 28, 30. In other embodiments, separator material 26 may instead or in addition be provided between the layers 27, 29, or not at all.

Any number of layers and sublayers may be provided as may be desirable in a particular embodiment of support layer 20. Certain embodiments include 4 layers and other embodiments include 8 layers. In general, 0-20 layers of three dimensional material are included in support layer 20.

Suitable three-dimensional materials for use in support layer 20 include a polyester weave such as Spacenet, manufactured by Freudenberg & Co. of Weinheim, Germany, Tytex, available from Tytex, Inc. of Rhode Island, U.S.A., and other woven, nonwoven, or knit breathable support materials or fabrics having resilient portions, microfilaments, monofilaments, or thermoplastic fibers. Other embodiments of support layers and suitable three dimensional materials are described in U.S. patent application Ser. No. 11/119,980, entitled PRESSURE RELIEF SUPPORT SURFACE, filed on the same date herewith, and assigned to the assignee of the present invention, the disclosure of which is incorporated herein by this reference.

Figure 5:
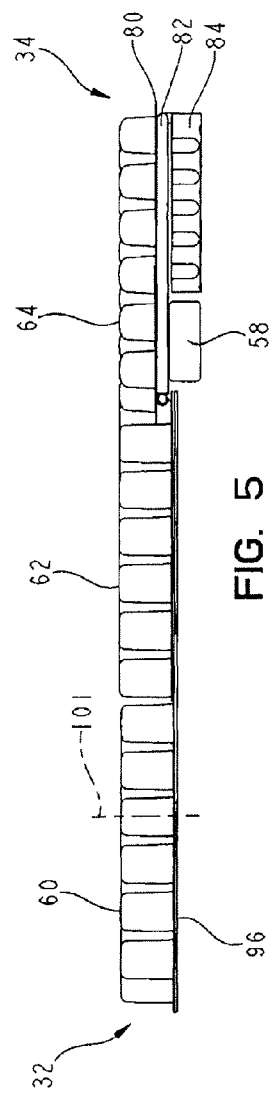
FIG. 5 is a side view of selected components of the illustrated embodiment of a patient support.

An exemplary second support layer including a base 96 and a plurality of inflatable bladders 50 is shown in the side view of FIG. 5. Inflatable bladders 50 extend upwardly away from base 96 along a vertical axis 101. Inflatable bladders 50 are arranged into a plurality of bladder zones, namely head bladder zone 60, seat bladder zone 62, and foot bladder zone 64. First and second foot filler portions 80, 84 and tube assembly 82 are located in the foot end 34 of patient support 10 below foot bladder assembly 64. Pneumatic valve box 58 is also located in foot end 34 of patient support 10 underneath foot bladder zone 64. In other embodiments, pneumatic box 58 may be located elsewhere in patient support 10 or outside patient support 10.

Figure 6:
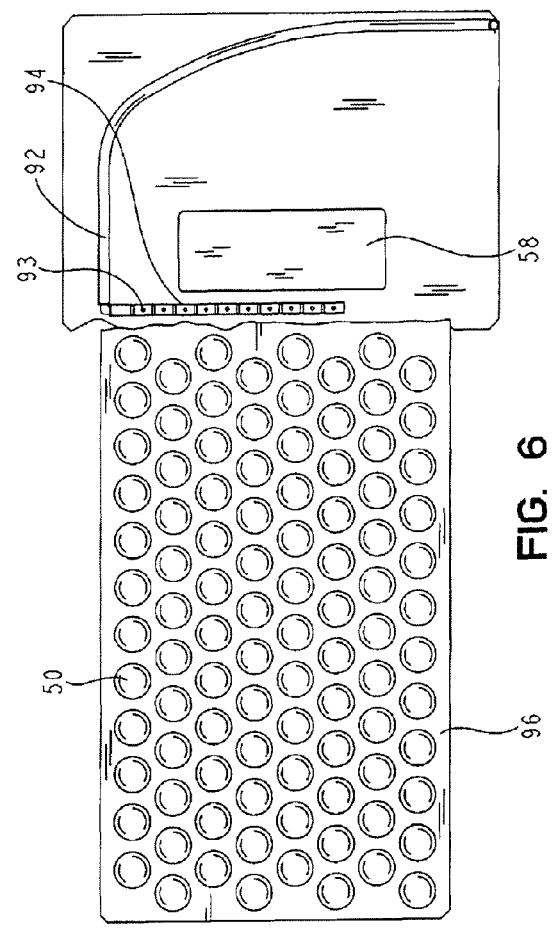
FIG. 6 is a top view of components of a patient support also shown in FIG. 5.

In FIG. 6, a top view of the above-described embodiment of patient support 10 is provided, with cover 12, support layer 20, and foot bladder assembly 64 removed to show the arrangement of delivery tube 92, air distributor 94, and pneumatic box 58 in the foot section 34. Pneumatic box 58 includes valves, circuitry, and other components for connecting vertical bladders 50 to an air supply 152 (FIG. 23) for inflation and deflation of vertical bladders 50. Pneumatic box 58 is described below with reference to FIGS. 25 and 26.

Delivery tube 92 is connected to an air supply and provides air to air distributor 94. In the illustrated embodiment, delivery tube extends transversely and/or diagonally across the width of patient support 10 and may be curved or angled toward seat section bladder zone 62. Tube 92 and distributor 94 are made of a lightweight air impermeable material such as plastic.

Air distributor 94 is coupled to an end of delivery tube 92 located near seat section bladder zone 62. Air distributor 94 is an elongated hollow member including one or more apertures 93 which allow air to exit the tube 92 and circulate among vertical bladders 50 and three-dimensional material 20. In certain embodiments, the air is directed upwardly through support layer 20. A vent (not shown) is provided in cover 12 to allow the circulated air to exit interior region 14. The vent is generally located on the opposite end of patient support 10 from the supply tube 92. An additional vent may be provided in the three-dimensional material enclosure, in embodiments where three-dimensional material 20 is enclosed in an enclosure within interior region 14 as discussed above. In those embodiments, the vent is also generally be located opposite the supply tube 92.

In the illustrated embodiment, air provided by delivery tube 92 does not bleed upwardly through cover 12, however, in other embodiments cover 12 may include a breathable or air permeable material allowing for air to flow upwardly through the cover 12 to the patient. Also, in other embodiments, a single supply tube is provided in place of delivery tube 92 and air distributor 94. While shown in the illustrated embodiment, the above-described air circulating feature is not necessarily a required component of the present invention.

Figure 7:
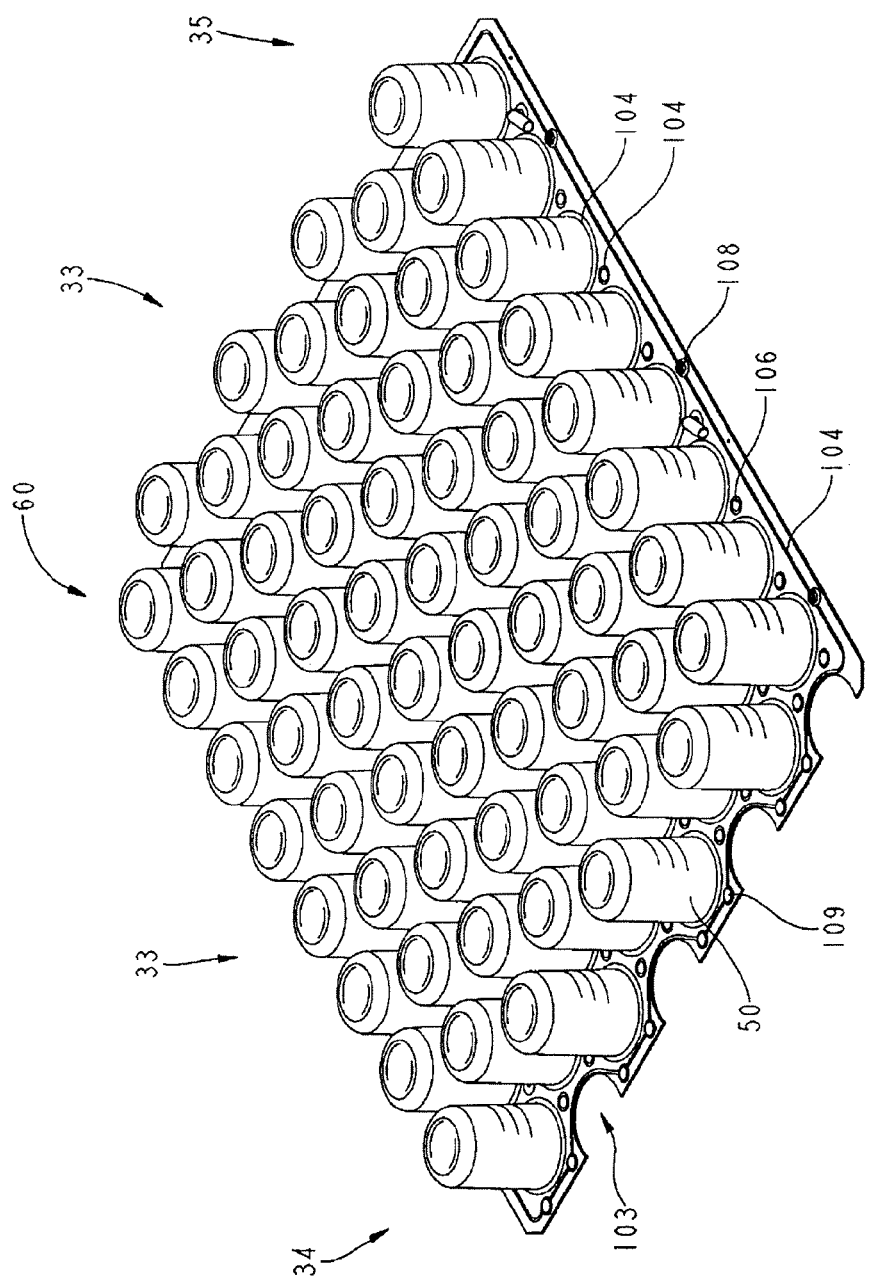
FIG. 7 is a perspective view of a first bladder assembly for a patient support.

Exemplary vertical bladder assemblies are shown in the perspective views of FIGS. 7, 14, 16, and 17. FIG. 7 illustrates a head section bladder assembly 60. Head section bladder assembly 60 includes a base or substrate 96 and a plurality of vertically-oriented inflatable bladders 50 extending upwardly from the base 96 along an axis 101 which is substantially perpendicular to base 96.

Head section bladder assembly 60 has a head end 32, a foot end 34, a first side 33 and a second side 35. Vertical bladders 50 are arranged in longitudinally-extending columns from head end 32 to foot end 34, and in transversely extending rows from first side 33 to second side 35.

Each bladder 50 is coupled to base 96 by a coupling 104. In the illustrated embodiment, radio frequency (RF) welding is used to couple bladders 50 to base 96. In other embodiments, other conventional coupling means, such as adhesives or sealants, may be used.

Figure 12A:
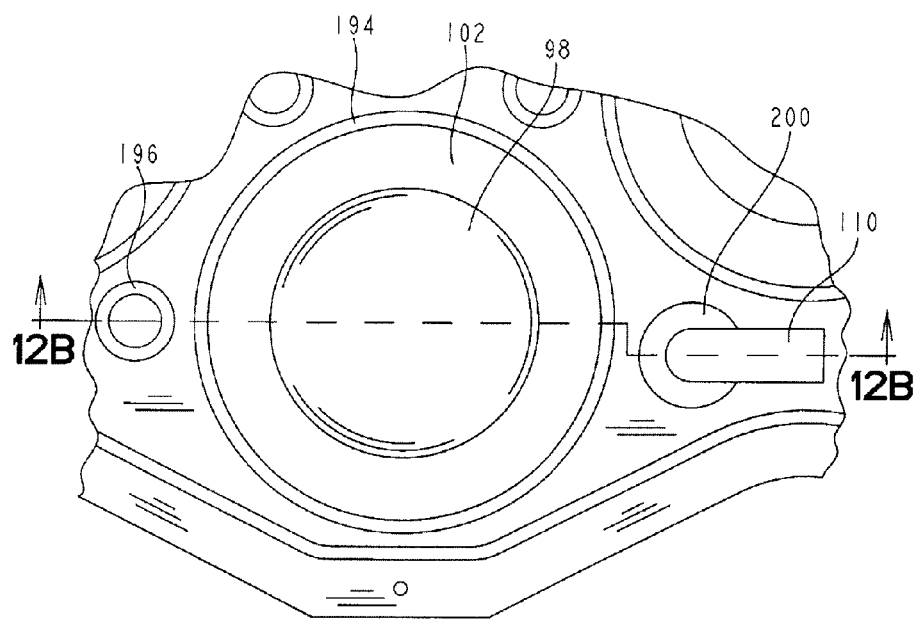
FIG. 12A is a top view of a portion of a bladder assembly including a vertical bladder and an inlet tube.
Figure 12B:
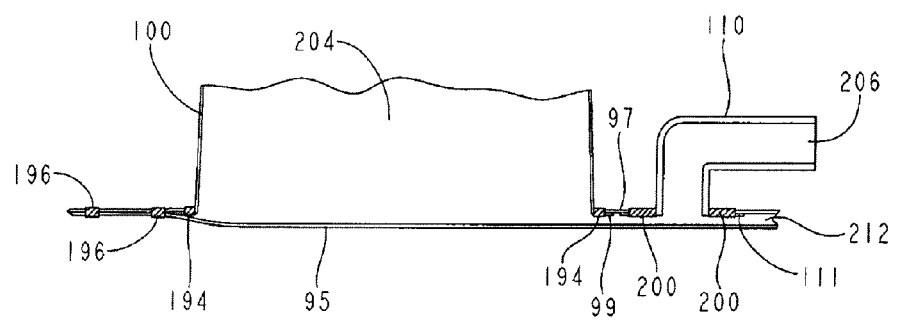
FIG. 12B is a cross-sectional view taken along line B-B of FIG. 12A.
Figure 12C:
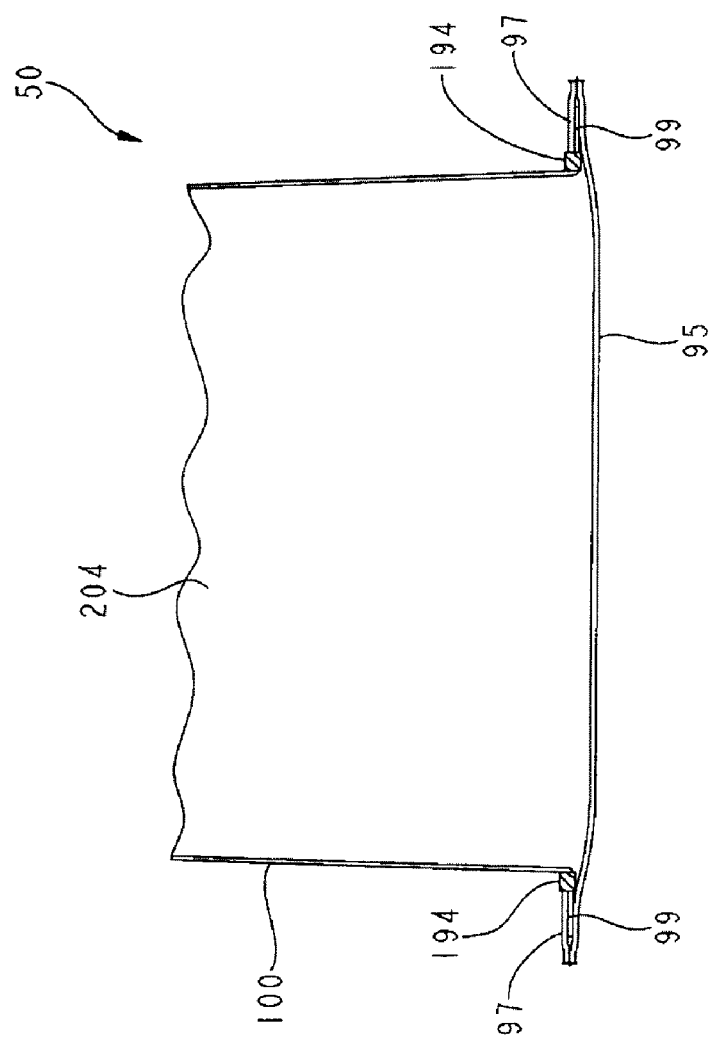
FIG. 12C is a cross-sectional view taken along line C-C of FIG. 9.
Figure 13:
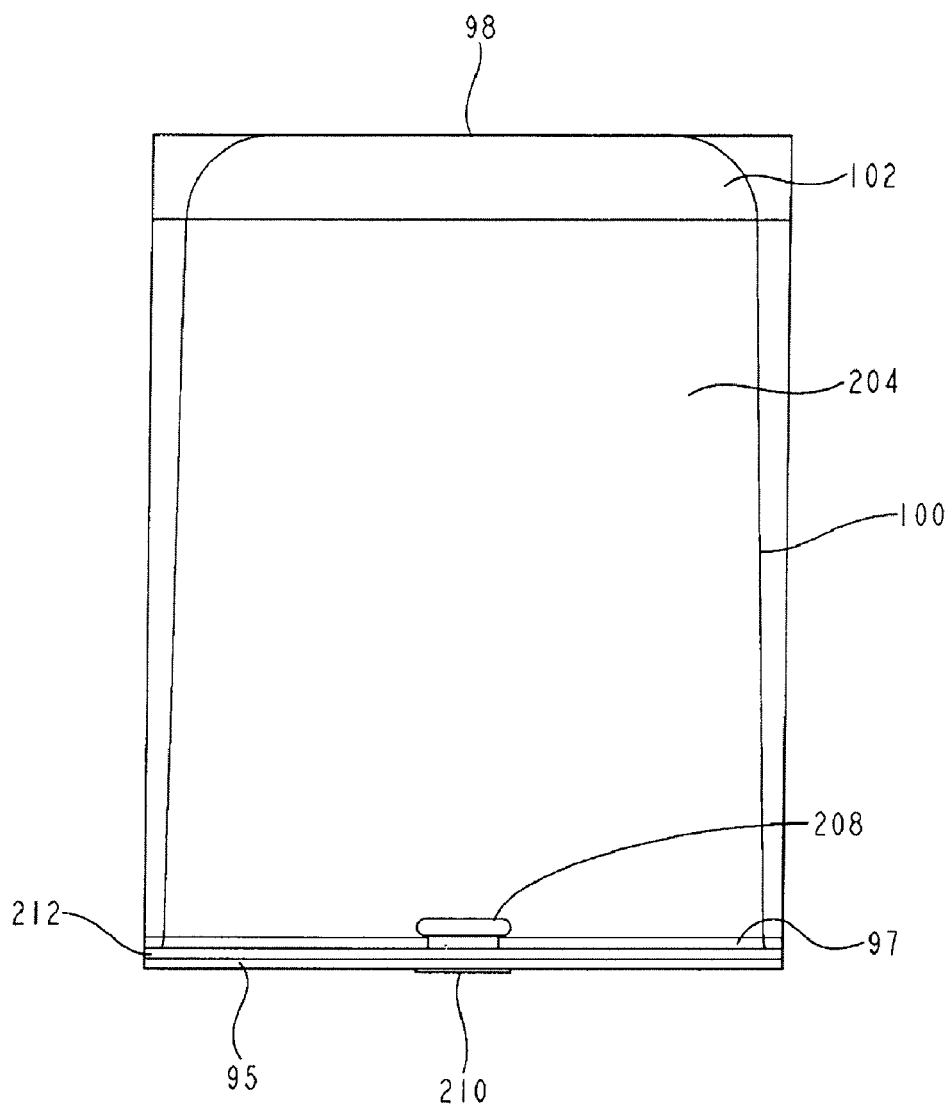
FIG. 13 is a cross-sectional view of a portion of a base and vertical bladder.

Base 96 includes an upper base portion or substrate 97 and a lower base portion or substrate 95 as best shown in FIGS. 12B, 12C and 13. Air channels 212 (best shown in FIG. 12B) are formed between upper base portion 97 and lower base portion 95 and provide air to bladders 50 from an air supply (FIG. 24B). Air release channels 206 are coupled to air channels 212 as shown in FIG. 12B.

Figure 16:
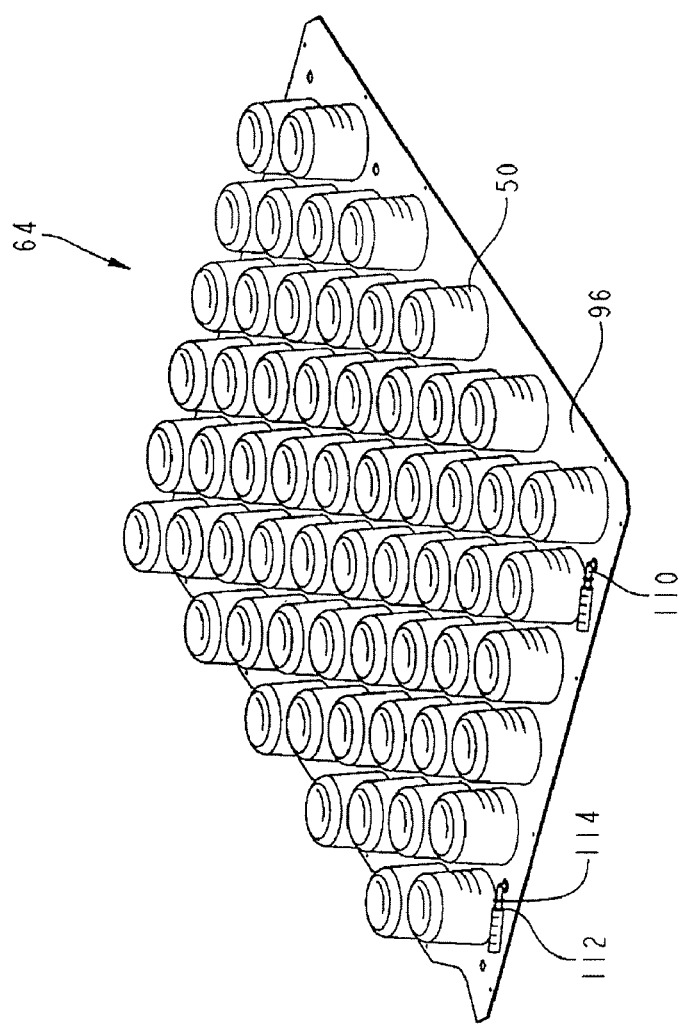
FIG. 16 is a perspective view of a third bladder assembly for a patient support.
Figure 17:
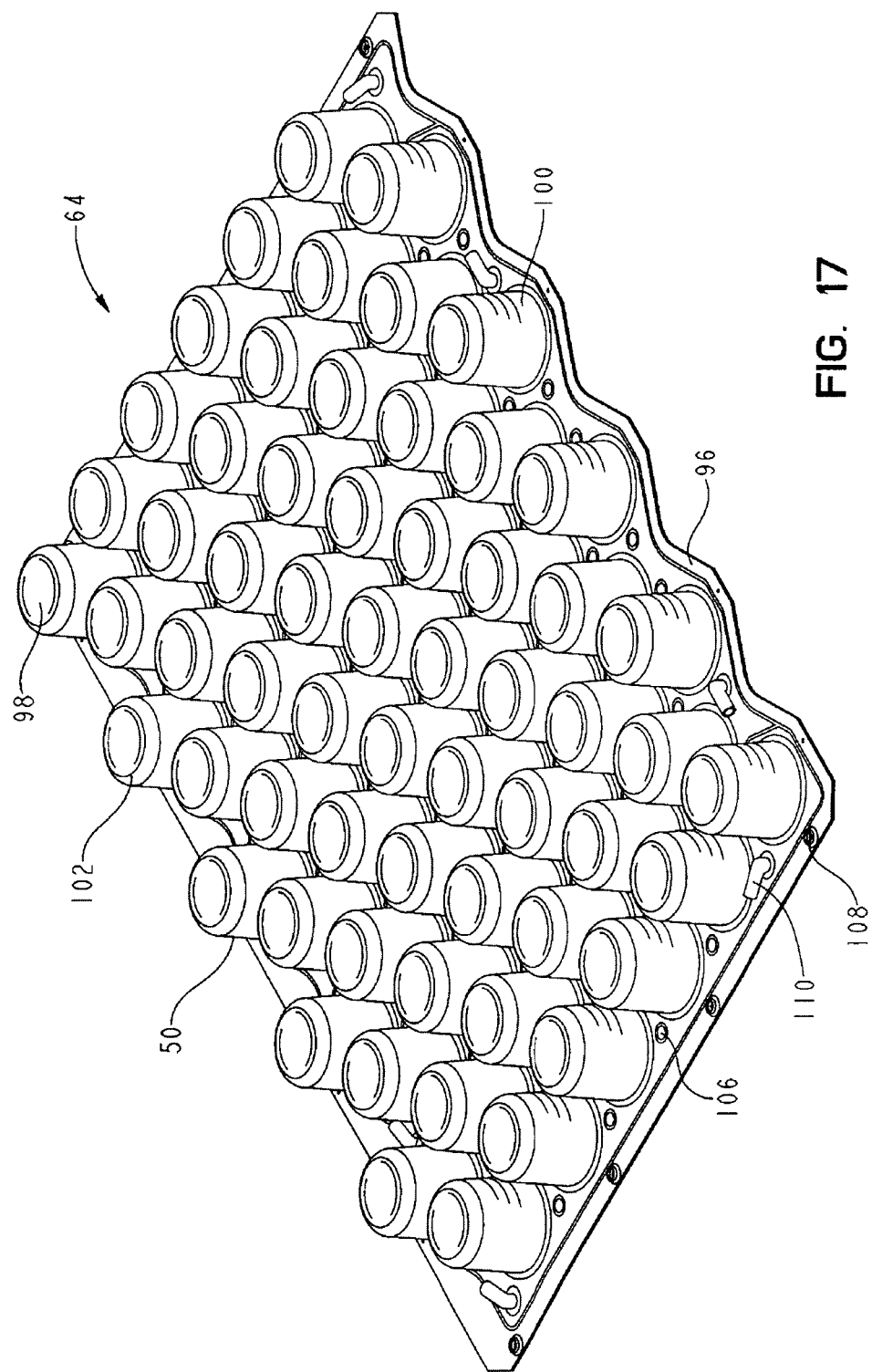
FIG. 17 is another perspective view of the bladder assembly of FIG. 16.

Elbow ports 110 and fittings 114 are coupled to air release channels 206 and to relief valves 112 as shown in FIG. 16. One suitable fitting 114 is a ½ inch by ⅜ inch barbed connector, model no. C8-6WN made of nylon, available from Eldon James Corp. of Loveland, Colo.

Pressure relief valves 112 release air to the atmosphere, for example, if the internal air pressure within the bladders 50 exceeds a maximum value. One suitable relief valve 112 is a 2.0 psi pressure relief valve model no. 730ROA available from Halkey-Roberts of St. Petersburg, Fla. In the illustrated embodiment, relief valves 112 are inserted into tubing such as ½-inch clear PVC tubing.

Returning now to FIGS. 7 and 9, upper base portion 97 is coupled to lower base portion 95 by welds 104, forming a plenum. Fasteners, 106, 108, 109 are generally spaced apart along the outer edges of base 96. Fasteners 106, 108, 109 secure the bladder assembly 60 within interior region 14, i.e. by coupling bladder assembly 60 to another bladder assembly, or to an inner portion of cover 12, or to stiffener plates 144, or to another component within interior region 14. As shown, fasteners 106 couple the bladder assembly 60 to the sensor pad 68, fasteners 108 couple bladder assembly 60 to support plate 144, and fasteners 109 couple bladder assembly 60 to bladder assembly 62. Fasteners 106, 108, 109 are, in the illustrated embodiment, plastic or metal buttons and snaps. However, other suitable fasteners, such as rivets, may also be used.

Elbow ports 110 are spaced apart and located along the edges of first and second sides 33, 35 of bladder assembly 60. In the illustrated embodiment, ⅜-inch ports 110 are provided on each side of bladder assembly 60 and at least one port is provided for each of head section assembly 60, seat section assembly 62, and foot section assembly 64.

Semi-circular regions 103 facilitate coupling of head section bladder assembly 60 with another bladder assembly, among other things. For instance, semi-circular regions 103 are sized to mate with vertical bladder portions of another bladder assembly, such as seat section bladder assembly 62.

Figure 8:
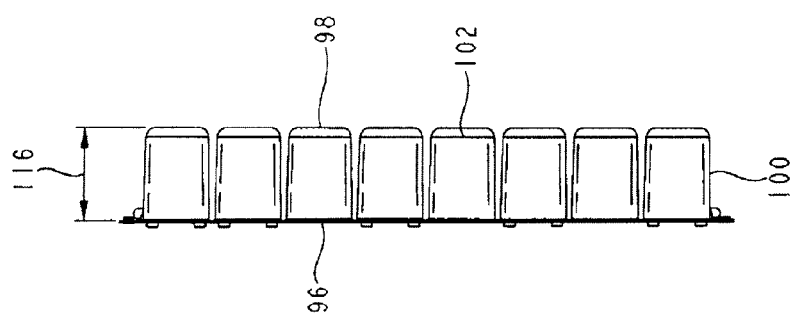
FIG. 8 is a side view of the bladder assembly of FIG. 7.

FIG. 8 is a side view of bladders 50 of head section bladder assembly 60. Bladders 50 each have a vertical portion 100, a top portion 98, and an angled or beveled portion 102 located in between the top portion 98 and the vertical portion 100. Each bladder 50 is coupled to base 96. Bladders 50 have a vertical height 116. In certain embodiments, vertical height 116 of bladders in the head section bladder assembly 60 is about 4 to about 6 inches. In one embodiment, vertical height 116 is about 4.9 inches and the height including plenum 95, 97 is about 6 inches.

Figure 9:
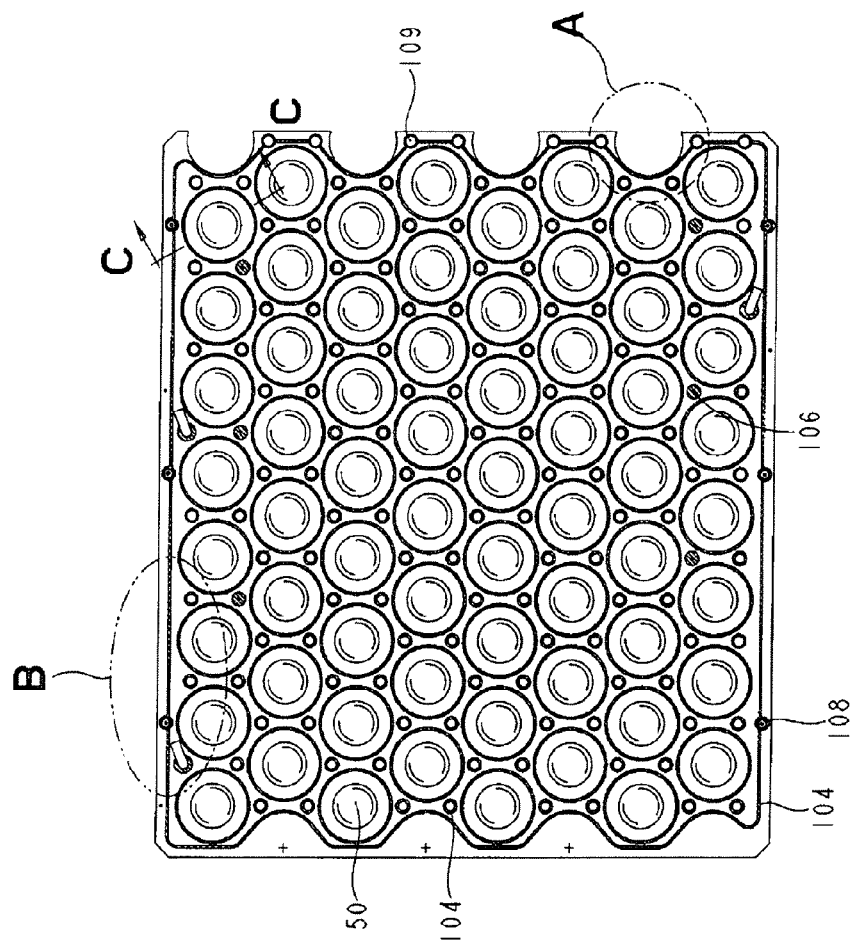
FIG. 9 is a top schematic view of the bladder assembly of FIG. 7.
Figure 11:
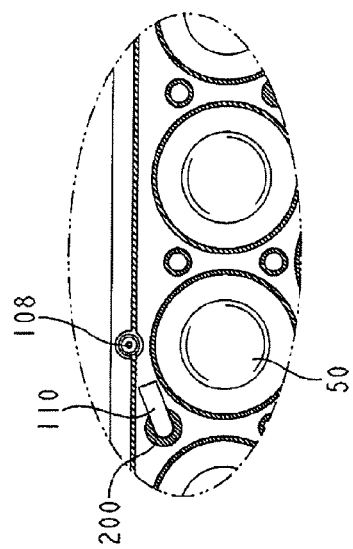
FIG. 11 is a close-up schematic view of Area B of FIG. 9.
Figure 10:
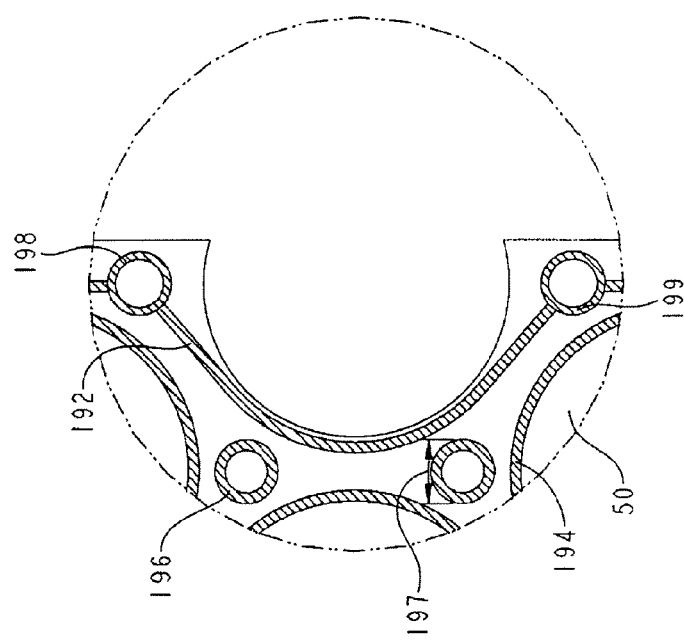
FIG. 10 is a close-up schematic view of Area A of FIG. 9.

FIG. 9 shows the pattern of couplings 104 (i.e., RF welds) used in the head section bladder assembly 60 of the illustrated embodiment of the present invention. Radio frequency welds 104 are provided around the circumference of each bladder 50, intermittently between the bladders 50 on the base 96, and along the outer edges of the bladder assembly. Welds 194 around the circumference of each bladder 50 couple coupling portion 99 of bladder 50 to upper base portion 97 as best shown in FIGS. 10, 11, 12B and 12C. Welds 196, 198 couple upper base portion 97 to lower base portion 95 as best shown in FIGS. 10, 11, and 12B. Dielectric welds 105 are used to join elbow ports 110 to upper base portion 95 as best shown in FIGS. 11 and 12B.

FIG. 10 is a close-up view of Area A of FIG. 9, showing outer edge welds 192, bladder welds 194, first circular welds 196, and second circular welds 198. In the illustrated embodiment, the welds 198 have an outer diameter 197 of about 4 inches and a thickness of about 0.125 inches; welds 196, 198 have an outer diameter of about 0.75 inches and a thickness of about 0.125 inches; and welds 192 have a thickness of about 0.125 inches. Other suitable weld configurations may be used without departing from the scope of the present invention. In some cases, circular welds 196, 198 may encircle fasteners 106, 108.

FIG. 11 additionally shows a weld 200 encircling an elbow port 110, which, as mentioned above, is done by dielectric welding.

FIG. 12A illustrates a portion of bladder assembly 60 including a weld 196, a bladder 50, and an elbow port 110. As discussed above, bladder 50 includes a top portion 98 and a beveled portion 102. Bladder 50 is substantially cone- or can-shaped or cylindrical in shape. However, in other embodiments, bladder 50 is square or cube-shaped, rectangular, hexagonal, octagonal, or any other suitable shape as will be understood by those of ordinary skill in the art. Welds 196, 194, and 200 are generally circular in shape. In the case of bladder weld 194, weld 194 is positioned along the circumference of bladder 50. In the case of weld 200, weld 200 is positioned along the circumference of elbow port 110.

FIG. 12B shows a cross sectional view of FIG. 12A taken along line 12B-12B. As shown in FIG. 12B, an air channel 212 supplies air from an air supply (not shown) to interior region 204 of bladder 50. Some of the air provided by air channel 212 resides in release channel 206. If the pressure in interior region 204, 206, 212 exceeds a maximum value, a pressure relief valve 112 coupled to channel 206 will release air to the atmosphere.

Air channel 212 is formed between upper base portion 97 and lower base portion 95, which are coupled together at welds 196. Upper base portion 97 includes a plurality of cut-out regions or holes (not shown) into which material forming bladders 50 is inserted. Each bladder 50 has an end portion 99 that is positioned between upper base portion 97 and lower base portion 95 as shown in FIGS. 12C and 13. End portion 99 is secured to upper base portion 97 by coupling or weld 194. Similarly, release channel 206 includes an end portion 111 which is secured to upper base portion 97 by coupling or weld 200.

In the illustrated embodiment, bladder 50 is thermoformed and only welded where end portion 99 meets upper base portion 97. In other embodiments, bladder 50 may be handcrafted; i.e., top portion 98 is welded to vertical portion 100 and vertical portion 100 also includes a welded seam.

Another cross-section of a portion of a bladder assembly 60 is shown in FIG. 13. FIG. 13 depicts an exemplary fastener 106, 108 suitable for coupling upper base portion 97 to lower base portion 95, and or for coupling base 96 to another surface (such as bottom surface of cover 12) within interior region 14. In the illustrated embodiment, each fastener 106, 108 includes a first fastener portion or stud 208 and a second fastener portion or post 210. In other embodiments, first fastener portion 208 is a button and second fastener portion 210 is a socket. In any case, first and second fastener portions 208, 210 are configured to mate with one another thereby coupling the intervening materials together.

FIG. 13 also illustrates air channel 212 located between upper and lower base portions 97, 95, vertical bladder wall 100 extending upwardly away from base 96, bladder top portion 98, and crown or bevel portion 102 located between top portion 98 and wall portion 100, defining an interior bladder region 204. In the illustrated embodiment, the diameter of each vertical bladder 100 is about 3.5". A smaller or larger diameter may be used in other embodiments.

Figure 14:
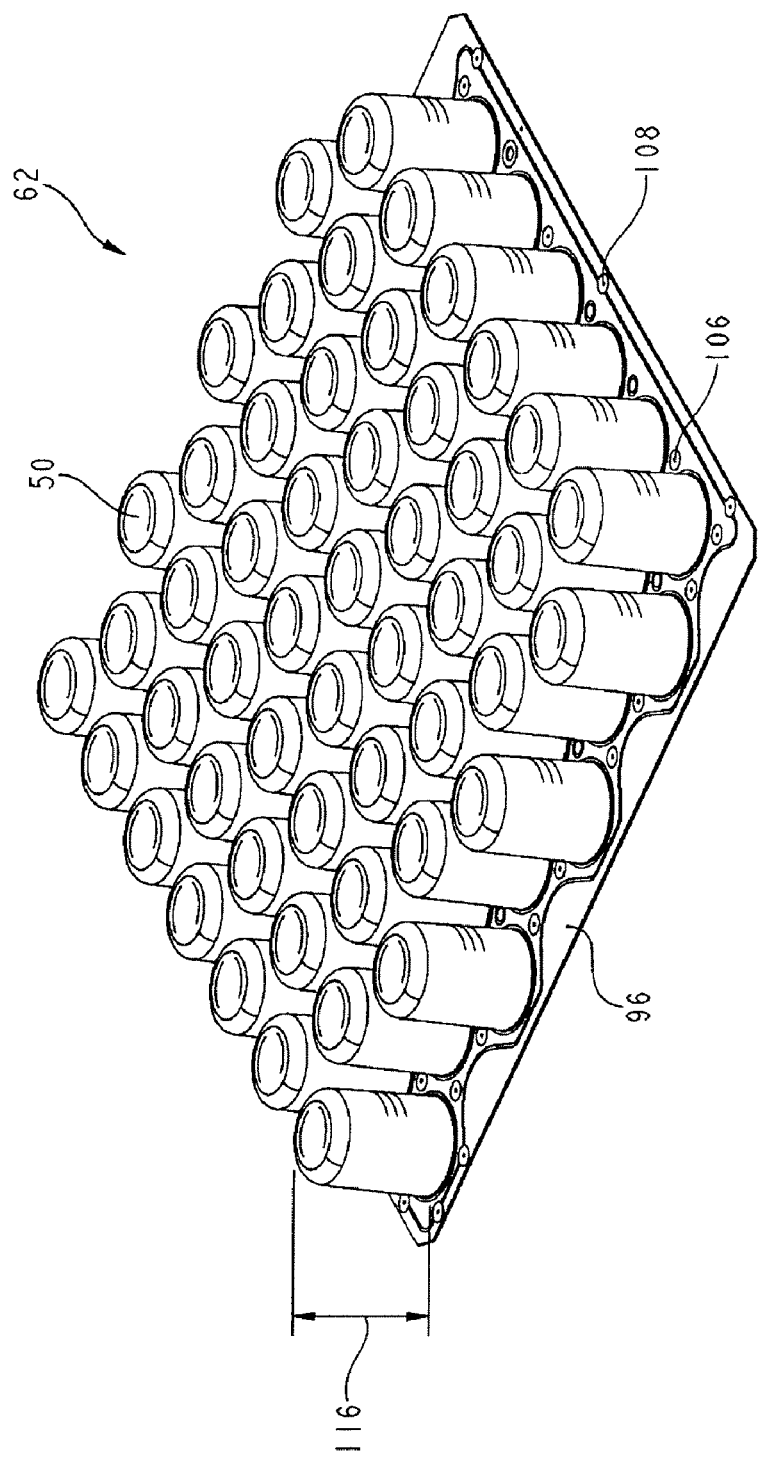
FIG. 14 is a perspective view of a second bladder assembly for a patient support.
Figure 15:
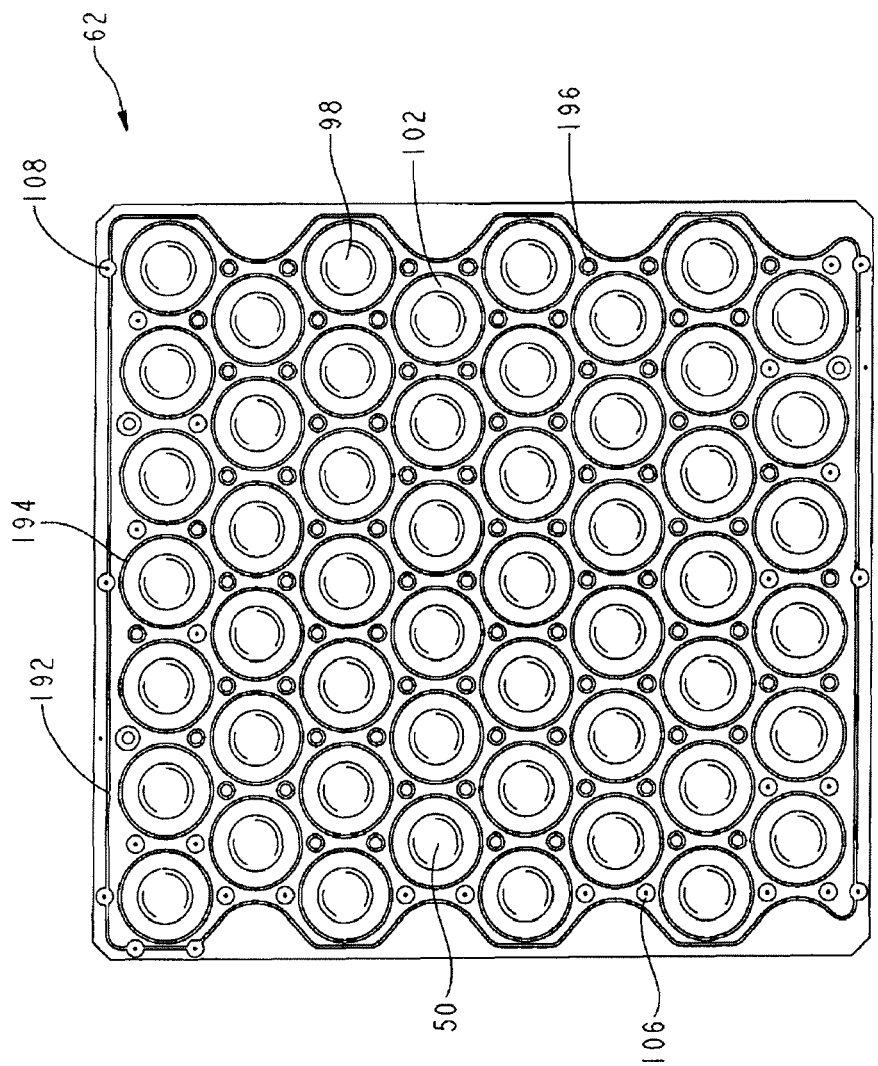
FIG. 15 is a top schematic view of the bladder assembly of FIG. 14.

FIGS. 14 and 15 depict an exemplary seat section bladder assembly 62. Seat section bladder assembly is generally configured to support a patient's seat, thighs, or midsection. The components of seat section bladder assembly 62 are substantially as described above with reference to head section bladder assembly 60. Bladders 50 of seat section bladder assembly 62 have a vertical height 116. In the illustrated embodiment, vertical height 116 is the same or about the same as vertical height 116 of the bladders in head section assembly 60.

Figure 18:
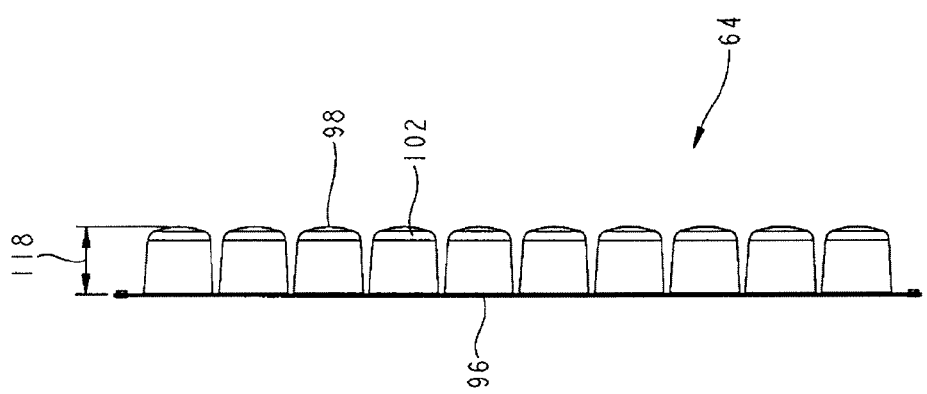
FIG. 18 is a side view of the bladder assembly of FIG. 16.

FIGS. 16-19 depict an exemplary foot section bladder assembly 64. Foot section bladder assembly 64 is generally configured to support a patient's legs and/or feet. The components of foot section bladder assembly 64 are substantially as described above with reference to head section bladder assembly 60. Bladders 50 of foot section bladder assembly have a vertical height 118 as shown in FIG. 18. In the illustrated embodiment, vertical height 118 is shorter or smaller than vertical height 116. In certain embodiments, vertical height 118 is about 2 to about 5 inches. In one embodiment, vertical height is about 3.5 inches and the height including plenum 95, 97 is about 4 inches.

Figure 19:
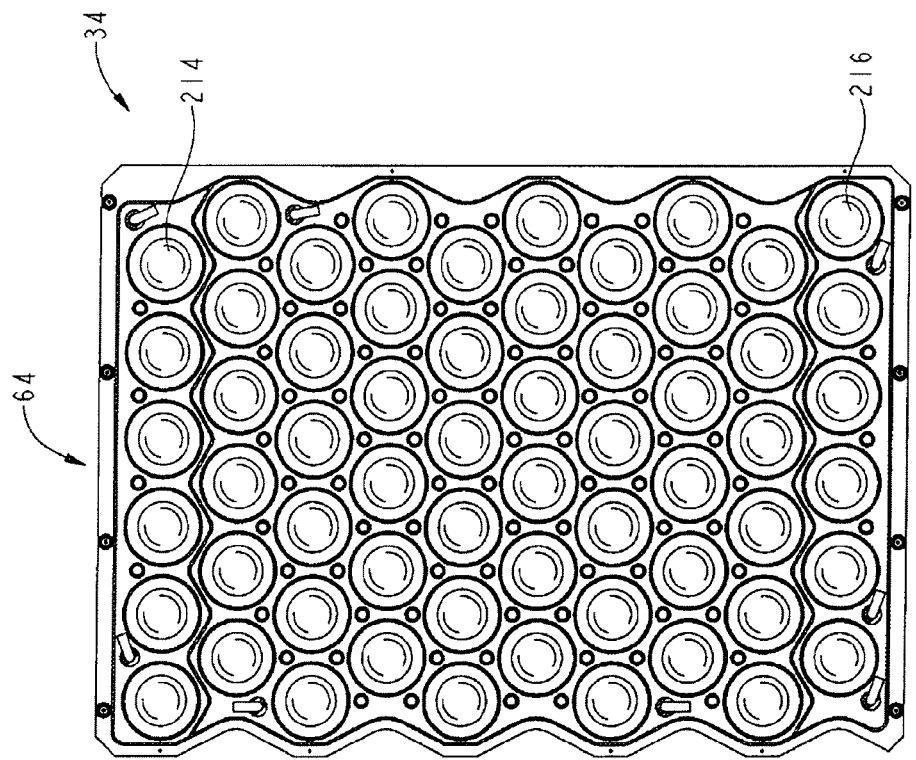
FIG. 19 is a top schematic view of the bladder assembly of FIG. 16.

As shown in FIG. 19, the illustrated embodiment of foot section bladder assembly 64 is wider than head and seat section bladder assemblies 60, 62. In this embodiment, foot section bladder assembly 64 includes longitudinal sections 214, 216, which may function as bolsters for the foot section. Longitudinal sections 214, 216 are separately inflatable from the remainder of the foot section 64, in the illustrated embodiment.

Figure 20:
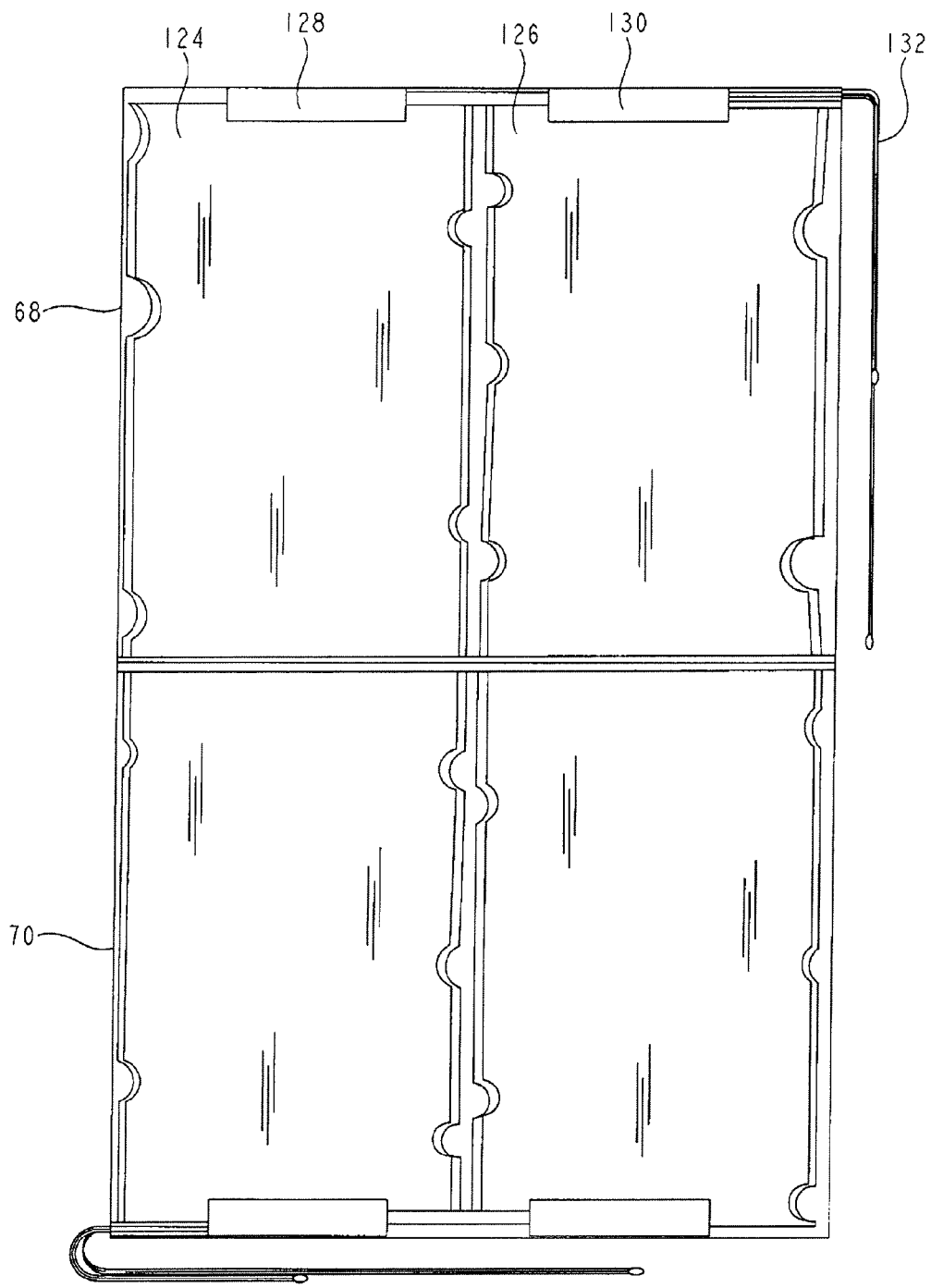
FIG. 20 is a top view of exemplary sensor pads.
Figure 21:
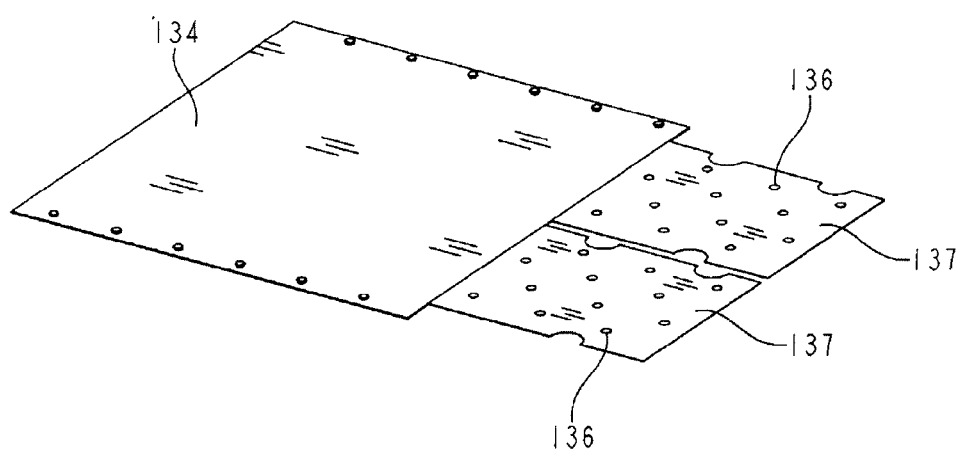
FIG. 21 is a perspective view of an exemplary sensor pad showing interior components thereof.

In the illustrated embodiment, patient support 10 includes a pressure sensing member 67 located underneath the bladder assemblies 60, 62, 64. As shown in FIG. 20, pressure sensing member 67 includes a first or head section sensor pad 68 and a second or seat section sensor pad 70. Further, each sensor pad 68, 70 includes first and second sensor pad portions 124, 126. Each sensor pad portion 124, 126 includes a plurality of pressure sensors 136 located on a substrate 220. Sensors 136 are designed to respond when pressure is applied to the top surface of patient support 10, i.e. by a patient. Sensors 136 are spaced apart and arranged on substrate 220 so that they are positioned adjacent or underneath or aligned with one or more vertical bladders 50. In the illustrated embodiment, a sensor 136 is positioned underneath the center or middle portion of each vertical bladder 50. Substrate 220 is made of a substantially rigid material such as plastic. An additional interface layer may be provided between base 96 and substrate 220 to direct applied force to sensors 136, or for other reasons. Sensors 136 include a soft or flexible material such as foam and one or more light conductors or optical fibers (not shown) located within the foam. Sensors 136 and substrate 137 are enclosed within a cover 22 as shown in FIG. 21.

The sensors 136 in each sensor pad 68, 70 are coupled to a collector/transmitter 128, 130, which receives pressure data from sensors 136 and transmits the data to a circuit located in pneumatic box 58 by communication lines 132. A collector/transmitter 128, 130 is located at one end of each sensor pad portion 124, 126.

In the illustrated embodiment, the pressure data obtained by sensors 136 is indicative of an amount of pressure being applied (i.e., by a patient or portion thereof being supported by patient support 10) to one or more vertical bladders 50. The pressure sensing apparatus 67 and components and operation thereof are described in more detail in U.S. patent application Ser. No. 11/119,991, titled PATIENT SUPPORT HAVING REAL TIME PRESSURE CONTROL, filed on the same date herewith and assigned to the assignee of the present invention, which is incorporated herein by this reference.

Figure 22:
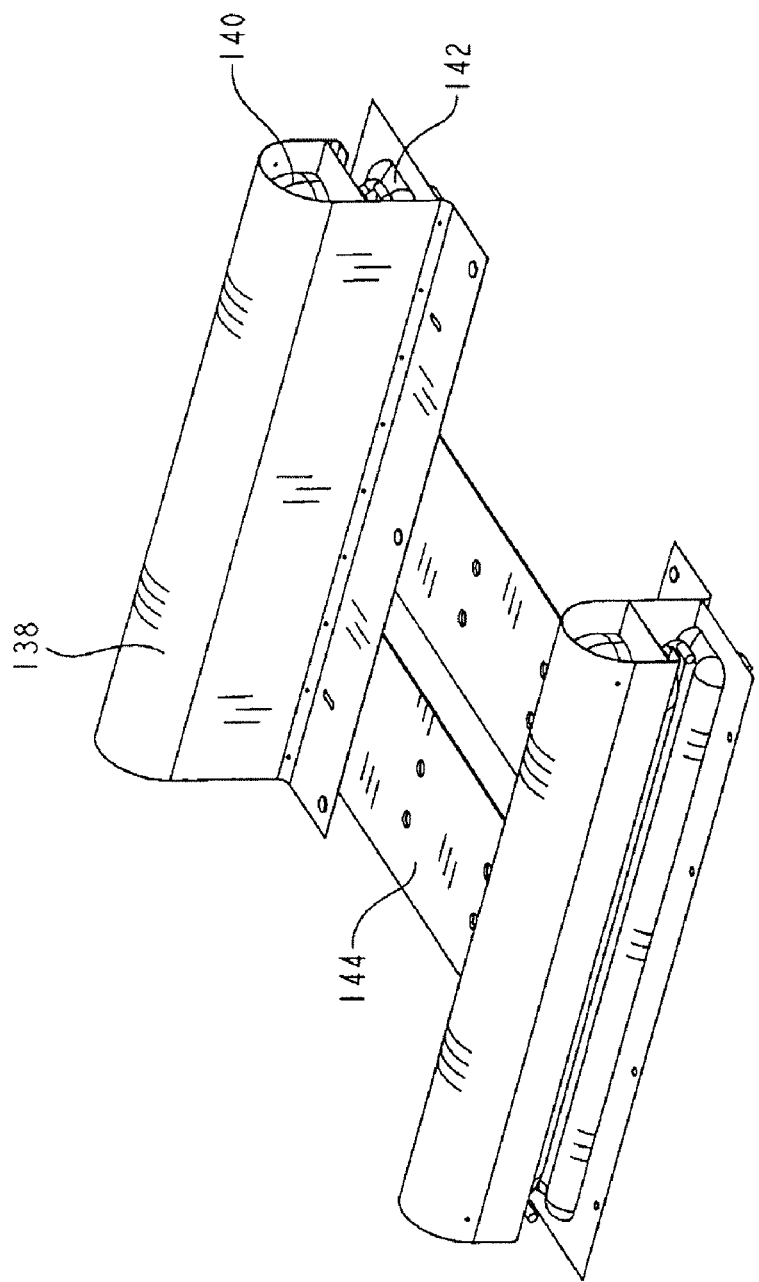
FIG. 22 is a perspective view of an exemplary bolster assembly.

FIG. 22 depicts a bolster assembly 76, 78. Bolster assemblies 76, 78 are generally configured to support portions of a patient along the longitudinal edges of patient support 10. One or more bolster assemblies 76, 78 may be provided in order to conform patient support 10 to a particular bed frame configuration, to provide additional support along the edges of patient support 10, aid in ingress or egress of a patient from patient support 10, maintain a patient in the center region of patient support 10, or for other reasons. For example, internal air pressure of the bolster bladders may be higher than the internal bladder pressure of assembles 60, 62, 64, or may be increased or decreased in real time, to accomplish one of these or other objectives.

Each bolster assembly 76, 78 includes a plurality of bolsters, namely, an upper bolster 140 and a lower bolster 142, with the upper bolster 140 being positioned above the lower bolster 142. Each upper and lower bolster combination 140, 142 is configured to be positioned along a longitudinal edge of patient support 10. Each upper and lower bolster combination 140, 142 is enclosed in a cover 138.

Figure 23:
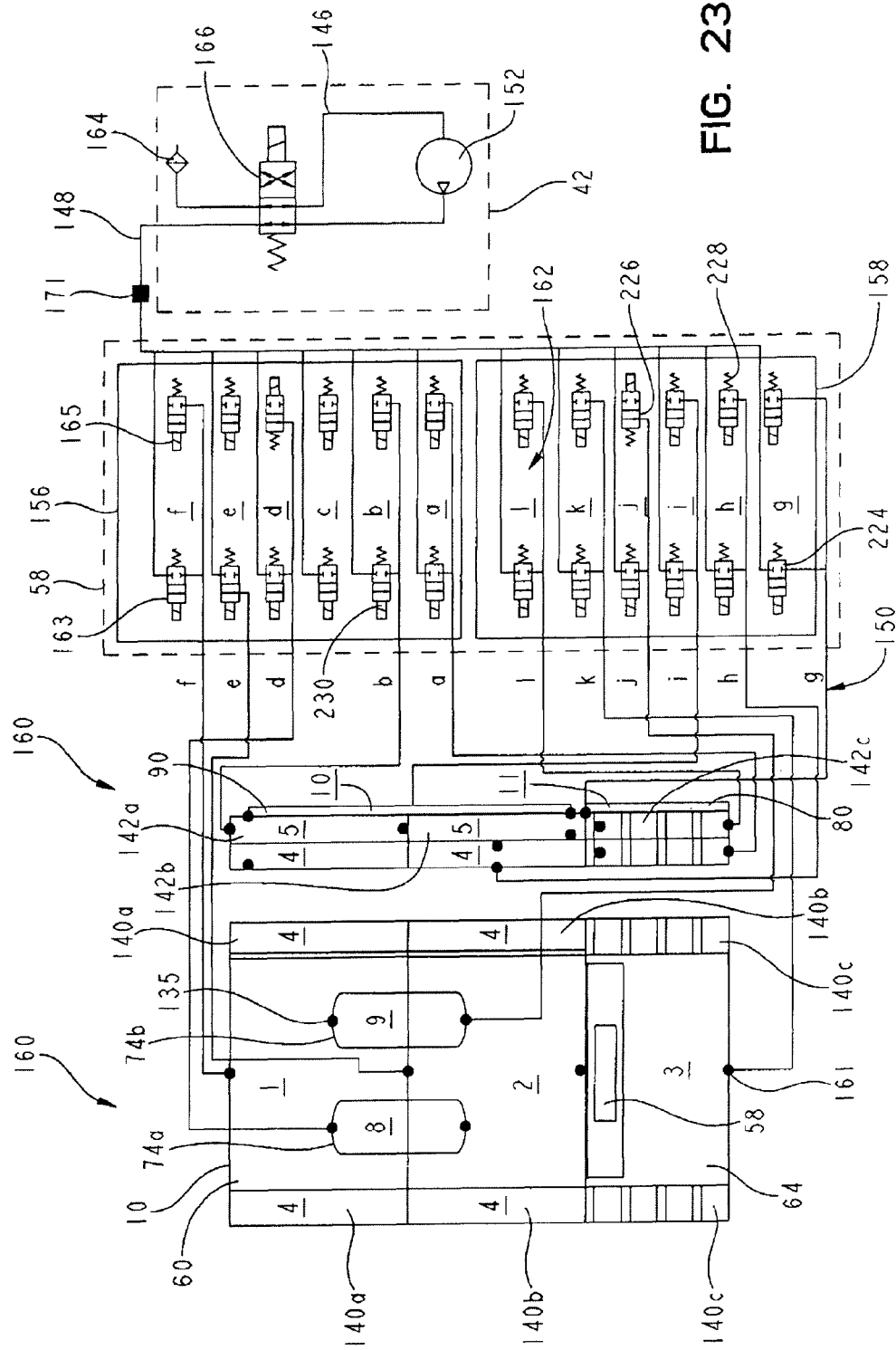
FIG. 23 is a schematic view of air zones of the illustrated patient support and associated air supply system.

In the illustrated embodiment, the bolsters 140, 142 are inflatable bladders. In other embodiments, either or both bolsters 140, 142 may be constructed of foam, or filled with three-dimensional material, fluid, or other suitable support material. For example, in one embodiment, upper bolster 140 includes two layers of foam: a viscoelastic top layer and a non visco elastic bottom layer, while lower bolster 142 is an inflatable bladder. The bolsters 140, 142 may be inflated together, or separately, as shown in FIG. 23, described below.

Each bolster combination 140, 142 is coupled to one end of one or more support plates 144 which provide support for other components of patient support 10 including vertical bladders 50. Support plates 144 may be made of a substantially rigid or stiff yet lightweight material such as molded plastic. In other embodiments, plates 144 may be constructed of stainless steel or steel, if additional weight is desired, i.e. for addition, collapsibility for ease of storage of patient support 10, for instance. Support plates 144 may be provided in order to give support to patient support 10 particularly during transport, for ease of assembly, or for other reasons.

In the illustrated embodiment, each support plate 144 is a rectangular member extending transversely across the width of the mattress 10. As shown in the drawings, there are five such rib-like members 144 spaced apart underneath the head and seat sections of the mattress. In other embodiments, each support plate 144 has its middle section (i.e., the section extending transversely) cut out so that only the two plate ends remain at each spaced-apart end (underneath the bolsters); thereby providing five pairs of support plates 144 spaced apart along the longitudinal length of the mattress 10.

Bolster assembly 86 is similar to bolster assemblies 76, 78 except that its upper layer includes the vertical bladders 50 of longitudinal sections 214, 216. Bolster assembly 86 has a longitudinally-oriented bladder as its lower bolster portion.

A schematic diagram of the pneumatic control system of patient support 10 is shown in FIG. 23. Reading FIG. 23 from second to first, there is shown a simplified top view of patient support 10 with portions removed to better illustrate the various air zones 160, a simplified side view of patient support 10, a schematic representation of pneumatic valve box 58, a schematic representation of control unit 42, and air lines 146, 148, 150 linking control unit 42, valve box 58, and air zones 160.

As shown in FIG. 23, air zones 160 of patient support 10 are assigned as follows: zone 1 corresponds to head section bladder assembly 60, zone 2 corresponds to seat section bladder assembly 62, zone 3 corresponds to foot section bladder assembly 64, zone 4 corresponds to upper side bolsters 140, zone 5 corresponds to lower side bolsters 142, zone 6 corresponds to upper foot bolsters 140, zone 7 corresponds to lower foot bolsters 142, zone 8 corresponds to first turn-assist bladder 74, zone 9 corresponds to second turn-assist bladder 74, zone 10 corresponds to deck filler 90, and zone 11 corresponds to foot filler 80.

An air line 150 couples each zone 160 to a valve assembly 162 in valve box 58. Valve box 58 is located in the foot section 34 of patient support 10. Illustratively, valve box 58 is releasably coupled to bottom portion 18 of cover 12 in interior region 14, i.e., by one or more Vecro®-brand fasteners or other suitable coupler.

Each air line 150 is coupled at one end to an inlet port 135 on the corresponding bladder or bladder assembly. Each air line 150 is coupled at its other end to a valve assembly 162. Each valve assembly 162 includes first or fill valve 163 and a second or vent valve 165. First valves 163 are coupled to air supply 152 of control unit 42 by air lines 148. First valves 163 thereby operate to control inflation of the corresponding zone 160 i.e. to fill the zone with air. Second valves 165 operate to at least partially deflate or vent the corresponding zone 160, for example, if the internal air pressure of the zone 160 exceeds a predetermined maximum, or if deflation is necessary or desirable in other circumstances (such as a medical emergency, or for transport of patient support 10).

Each valve 163, 165 has an open mode 224 and a closed mode 226, and a switching mechanism 228 (such as a spring) that switches the value from one mode to another based on control signals from control unit 42. In closed mode 226, air flows from air supply 152 through the value 163 to the respective zone 160 to inflate the corresponding bladders, or in the case of vent valves 165, from the zone 160 to atmosphere. In open mode 228, no inflation or deflation occurs.

In the illustrated embodiment, an emergency vent valve 230 is provided to enable quick deflation of turning bladders 74 which draws air from atmosphere through a filter 164 and also vents air to atmosphere through filter 164. Air supply 152 is an air pump, compressor, blower, or other suitable air source.

Air supply 152 is coupled to a switch valve 155 by air line 146. Switch valve 166 operates to control whether inflation or deflation of a zone occurs. An optional proportional valve 171 may be coupled to air line 148 to facilitate smooth inflation or deflation of turn-assist bladders 74, or for other reasons.

In the illustrated embodiment, valve box 58 includes a first valve module 156 and a second valve module 158. First valve module 156 includes valves generally associated with a patient's first side (i.e., first side, from the perspective of a patient positioned on patient support 10) and second valve module 158 includes valves generally associated with a patient's second side (i.e., second side).

The various zones 160 are separately inflatable. Certain of the zones 160 are inflated or deflated to allow patient support 10 to conform to different bed frame configurations. For example, the deck filler 90 (zone 10 in FIG. 23) is inflated to conform patient support 10 to certain bed frame configurations, such as step deck configurations including the Total-Care® and CareAssist® bed frames, made by Hill-Rom, Inc., the assignee of the present invention, but is deflated when patient support 10 is used with a flat deck bed frame, such as the Advanta® bed made by Hill-Rom, Inc. As another example, the foot filler 80 (zone 11 in FIG. 23) is inflated when patient support 10 is used with the VersaCare®, Total-Care®, or CareAssist® beds, but the lower side bolsters 142 (zone 5 in FIG. 23) are not inflated when patient support 10 is used with a VersaCare® bed. As still another example, the lower foot bolsters 142 (zone 7 in FIG. 23) are inflated when patient support 10 is used on flat decks or other bed frames, including the Advantag and VersaCare® bed frames made by Hill-Rom, Inc.

Figure 24A:
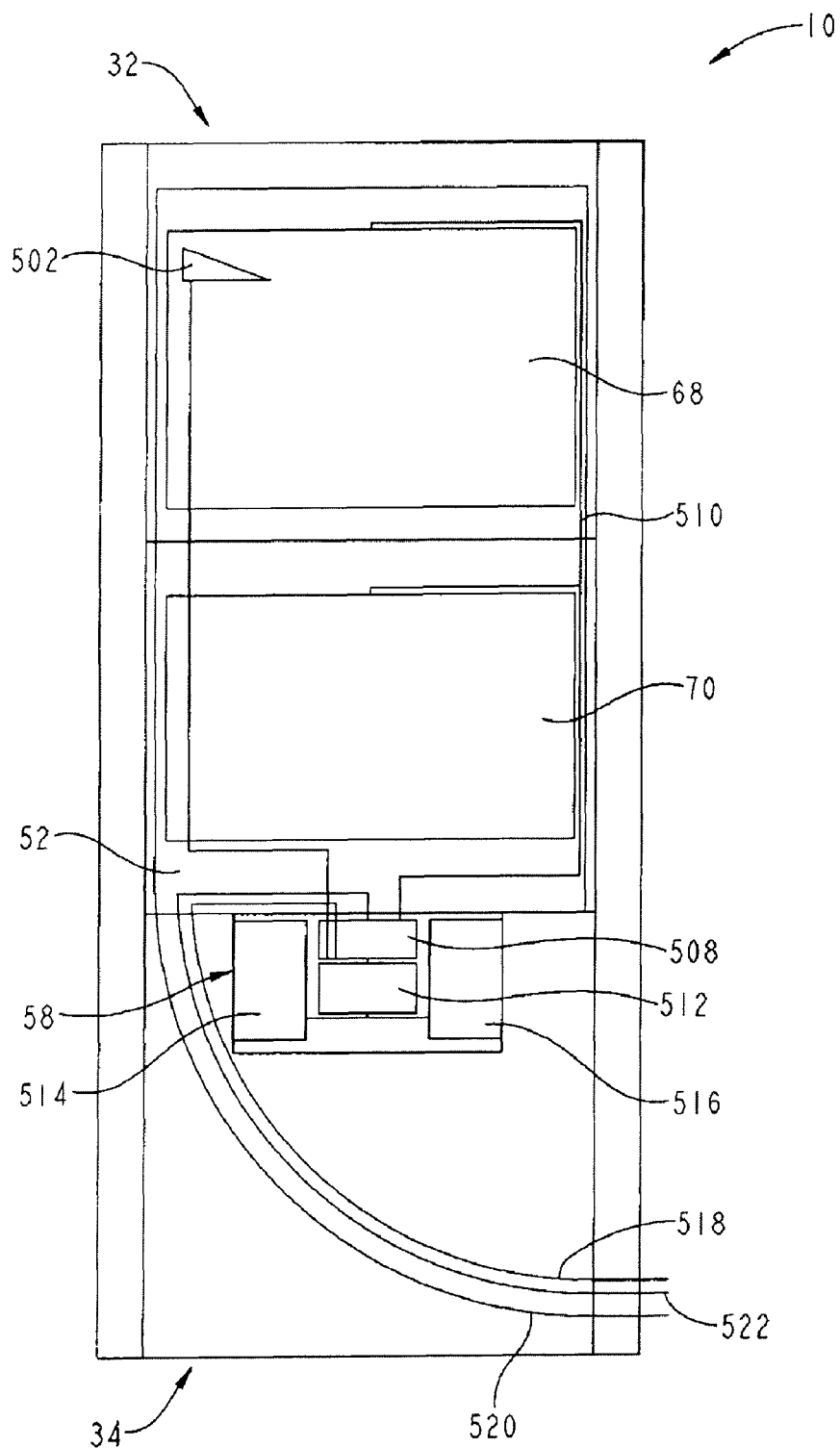
FIGS. 24A and 24B are schematic diagrams of portions of a control system for the illustrated patient support.
Figure 24B:
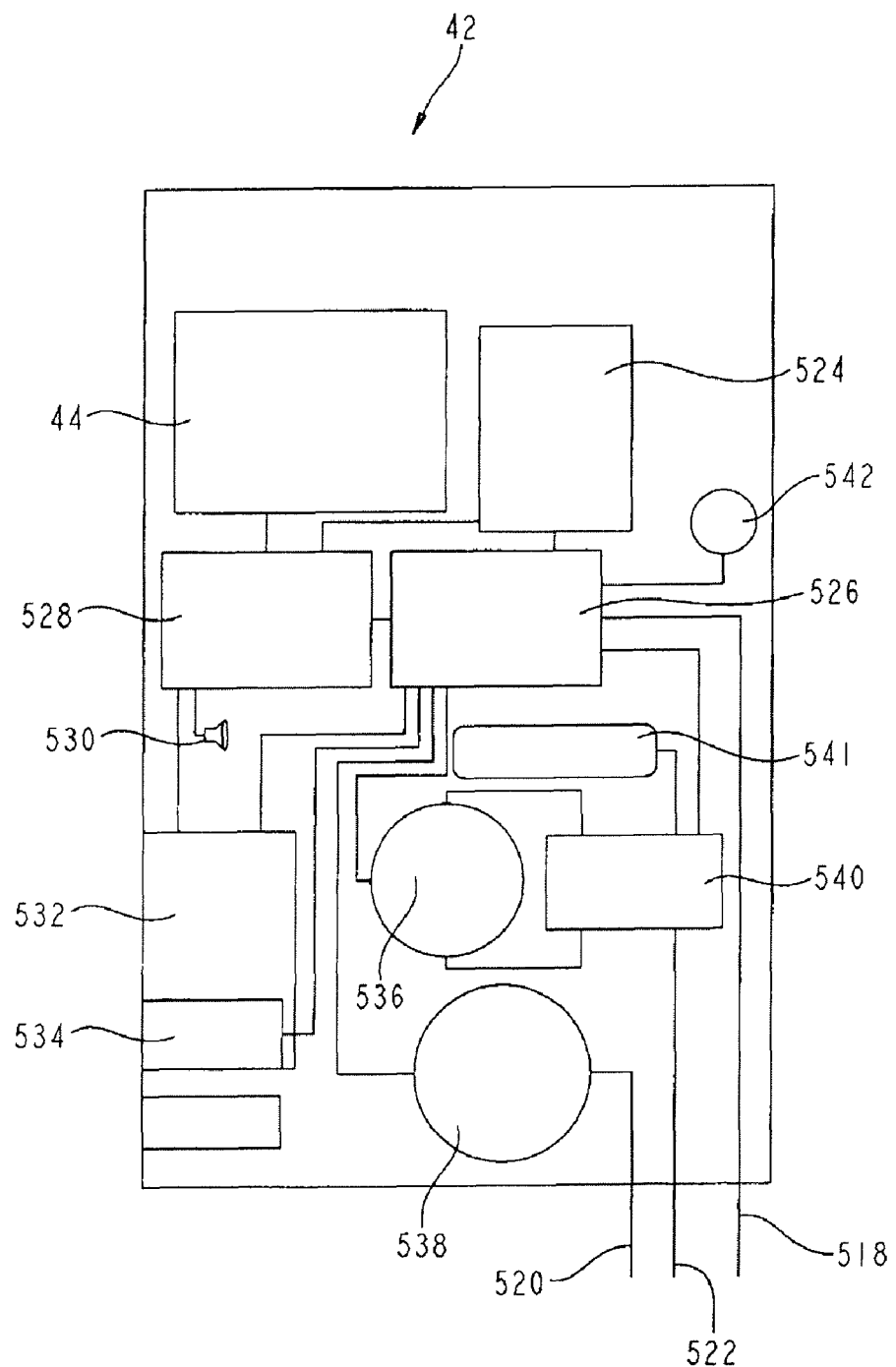

FIGS. 24A and 24B are a simplified schematic diagram of a control system and the patient support or mattress 10 of the present invention. FIG. 24A illustrates the patient support 10 including the various components of patient support 10 whereas FIG. 24B illustrates the control unit 42 and various components therein. The patient support 10 includes the sensor pad 52 which is coupled to the pneumatic valve control box 58 as previously described. The sensor pad 52 includes a head sensor pad 68 and a seat sensor pad 70. The head sensor pad 68 is located at the head end 32 of the mattress 10. The seat sensor pad 70 is located at a middle portion of the mattress 10 which is located between the head end 32 and a location of the pneumatic valve control box 58. The seat sensor pad 70 is located such that a patient laying upon the mattress 10 may have its middle portion or seat portion located thereon when in a reclined state. In addition, when the head end 32 of the mattress 10 is elevated, the seat portion of the patient is located upon the seat sensor pad 70. As previously described with respect to FIG. 3, the head sensor pad 68 is located beneath the head section bladder assembly 60 and the seat sensor pad 70 is located beneath the seat section bladder assembly 62. Each one of the sensors of the head sensor pad 68 or the seat sensor pad 70 is located beneath on at least adjacent to one of the upstanding cylindrical bladders or cushions 50. A head angle sensor 502 is coupled to the control box 58 where signals received from the sensor 52 may provide head angle information and pressure adjustment information for adjusting pressure in the seat bladders 62.

The sensor pad 52 is coupled through the associated cabling to the pneumatic control box 58. The pneumatic control box 58 includes a multiplexer 508 coupled to the head sensor pad 68 and the seat sensor pad 70 through a signal and control line 510. The multiplexer board 508 is also coupled to an air control board 512 which is in turn coupled to a first valve block 514 and a second valve block 516. A communication/power line 518 is coupled to the control unit 42 of FIG. 24B. Likewise, a ventilation supply line 520 which provides for air flow through the patient support 10 for cooling as well as removing moisture from the patient is also coupled to the control unit 42 of FIG. 24B. An air pressure/vacuum supply line 522 is coupled to the control unit 42 as well.

The control unit 42 of FIG. 24B, also illustrated in FIG. 1, includes the display 44, which displays user interface screens, and a user interface input device 524 for inputting to the control unit 42 user selectable information, such as the selection of various functions or features of the present device. The selections made on the user interface input device 524 control the operation of the patient support 10, which can include selectable pressure control of various bladders within the mattress 10, control of the deck 6, for instance to put the bed 2 in a head elevated position, as well as displaying the current state of the mattress or deck position, and other features.

An algorithm control board 526 is coupled to the user interface input device 524. The algorithm control board 526 receives user generated input signals received through the input device 524 upon the selection of such functions by the user. The input device 524 can include a variety of input devices, such as pressure activated push buttons, a touch screen, as well as voice activated or other device selectable inputs. The algorithm control board 526 upon receipt of the various control signals through the user input device 524 controls not only the operation of the mattress 10 but also a variety of other devices which are incorporated into the control unit 42. For instance, the algorithm control board 526 is coupled to a display board 528 which sends signals to the display 44 to which it is coupled. The display board 528 is also connected to a speaker 530 which generates audible signals which might indicate the selection of various features at the input device 24 or indicate a status of a patient positioned on patient support (e.g. exiting) or indicate a status of therapy being provided to the patient (e.g., rotational therapy complete). The algorithm control board 526 receives the required power from power supply 532 which includes an AC input module 534, typically coupled to a wall outlet within a hospital room.

The algorithm control board 526 is coupled to an air supply, which, in the illustrated embodiment includes a compressor 536 and a blower 538. Both the compressor 536 and the blower 538 receive control signals generated by the algorithm control board 526. The compressor 536 is used to inflate the air bladders. The blower 538 is used for air circulation which is provided through the ventilation supply line 520 to the mattress 10. It is, however, possible that the compressor 536 may be used to both inflate the bladders and to circulate the air within the mattress 10. A pressure/vacuum switch valve 540 is coupled to the compressor 536 which is switched to provide for the application of air pressure or a vacuum to the mattress 10. A muffler 541 is coupled to the valve 540. In the pressure position, air pressure is applied to the mattress 10 to inflate the mattress for support of the patient. In the vacuum position, the valve 540 is used to apply a vacuum to the bladders therein such that the mattress may be placed in a collapsed state for moving to another location or for providing a CPR function, for example. A CPR button 542 is coupled to the algorithm control board 526.

As illustrated, the algorithm control board 526, the compressor 536, the blower 538, and the user input device or user control module 524 are located externally to the mattress and are a part of the control unit 42, which may be located on the footboard 38 as shown in FIG. 1. The sensors and sensor pad 52, the pneumatic valve control box 58, and the air control board or microprocessor 512 for controlling the valves and the sensor pad system 52 are located within the mattress 10. It is within the present scope of the invention to locate some of these devices within different sections of the overall system, for instance, such that the algorithm control board 526 could be located within the mattress 10 or the air control board 512 could be located within the control unit 42.

Figure 25:
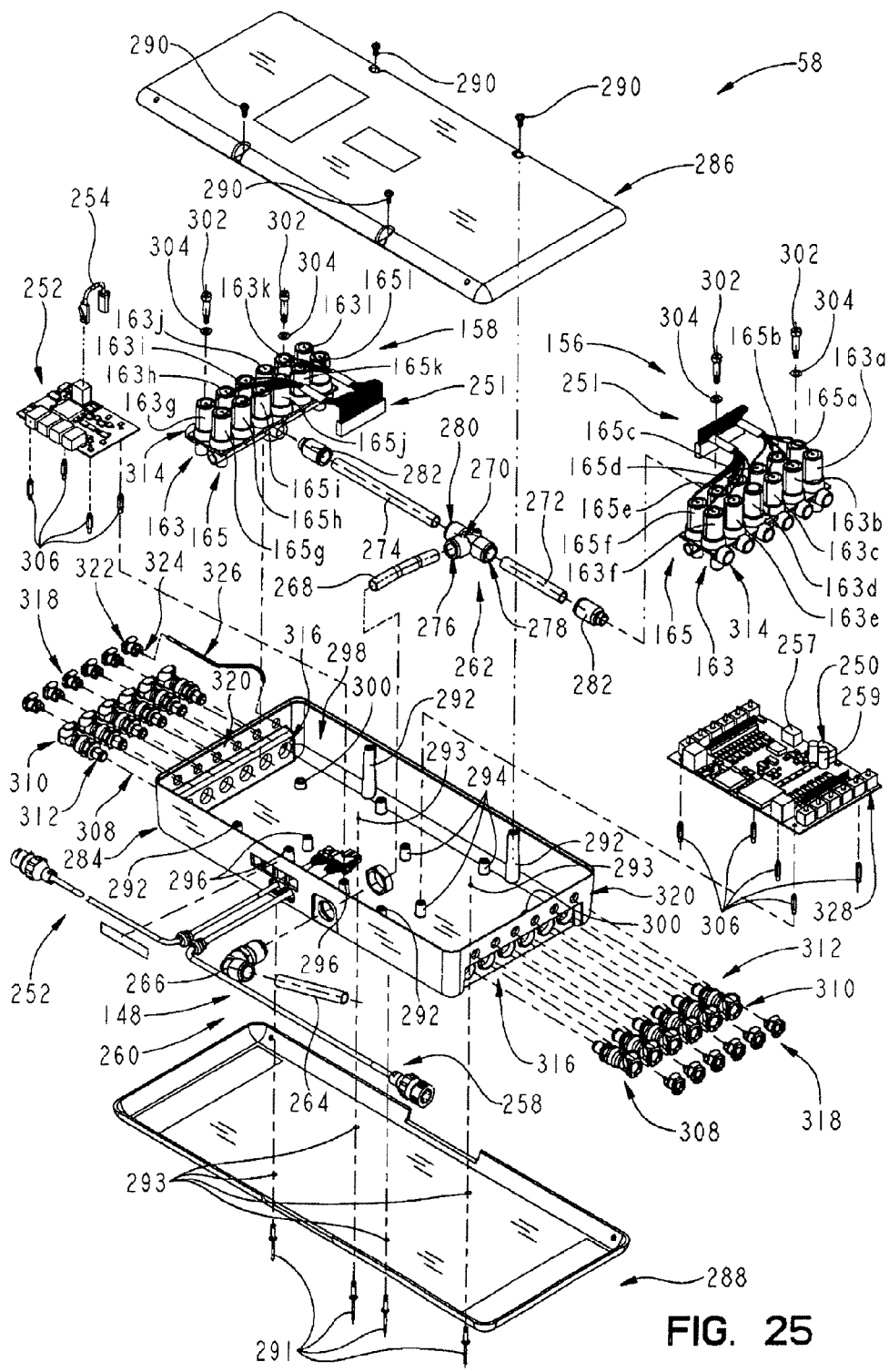
FIG. 25 is an exploded view of an exemplary pneumatic assembly.
Figure 26:
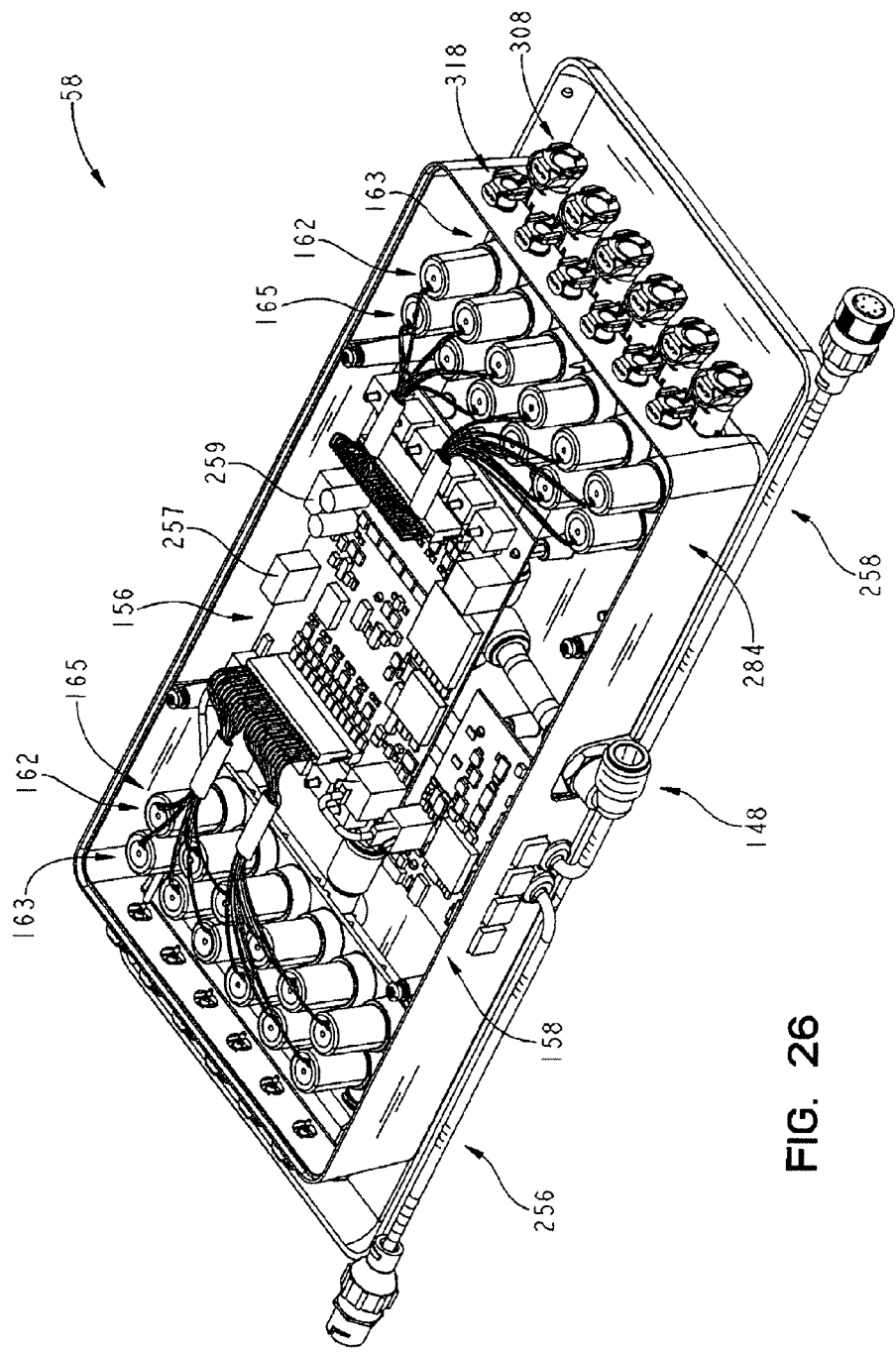
FIG. 26 is a perspective view of the pneumatic assembly of FIG. 25.

As shown in FIGS. 25-26, control box 58 includes a multiplexer 252 and an air control board 250. Control board 250 is coupled to multiplexer 252 by a jumper 254. Multiplexer 252 is further coupled to head sensor pad 68 and seat sensor pad 70 through a signal and control line (not shown). Control board 250 is also coupled to first valve module 156 and second valve module 158 by wire leads 251. A communication/power line 258 couples control board 250 to the control unit 42. Communication line 258 couples to a communication plug 259 of control board 250. Jumper 254 couples multiplexer 252 to control board 250 for power and access to communication line 258. Wire leads 251 provide actuation power to first and second valve modules 156, 158.

An angle sensor cable 256 is provided to send a signal from a head angle sensor 502 to the control board 250. Angle sensor cable 256 couples to an angle plug 257 of control board 250. In the illustrated embodiment, head angle sensor 502 is located within head bolster assembly 76 as indicated by FIG. 24A. Head angle sensor 502 indicates the angle of elevation of the head end 32 of bed 2 as the head section of the frame 4 articulates upwardly raising the patient's head or downwardly lowering the patient's head. In one embodiment, angle sensor 502 transmits the angle of head end 32 to all nodes or circuit boards within the mattress control system 42, 58. Angle sensor 502 generates an indication or indicator signal when head end 32 is at an angle of at least 5°, at least 30°, and at least 45°. The head angle indication is transmitted to the control unit 42 which evaluates and processes the signal. When head end 32 is at an angle above 30° turn assist 74 becomes inoperative primarily for patient safety reasons. When head end 32 is at an angle above 45° information is transmitted to control unit 42 for use in the algorithms. The 5° angle indication is primarily to ensure relative flatness of patient support 10. In the illustrated embodiment, angle sensor 502 is a ball switch or string potentiometer.

As discussed above, first and second valve modules 156, 158 include fill valves 163 and vent valves 165. First valve module 156 includes fill valves 163*a-f* and vent valves 165*a-f*. Second valve module 156 includes fill valves 163*g-l* and vent valves 165*g-l*. Fill valves 163*a-l* and vent valves 165*a-l* are 12 Volt 7 Watt solenoid direct active poppet style valves in the illustrated embodiment. Control board 252 is able to actuate each fill valve 163a-l and vent valve 165a-l independently or simultaneously. Fill valves 163a-l and vent valves 165a-l are all able to be operated at the same time. In operation to initiate each valve 163, 165, control board 250 sends a signal to the valve to be operated. The signal causes a coil (not shown) within each valve to energize for ½ second and then switches to pulsate power (i.e., turn on and off at a high rate) to save power during activation. The activation in turn cause the valve to either open or close depending on which valve is initiated.

Fill valves 163 are coupled to air supply 152 of control unit 42 by second air line 148. Air line 148 includes an outer box line assembly 260 and an inner box line assembly 262. Outer box line assembly 260 includes an exterior inlet hose 264 and an elbow 266 coupled to exterior inlet hose 264. Inner box line assembly 262 includes an interior inlet hose 268 coupled to elbow 266, a union tee connector 270, a first module hose 272, and a second module hose 274. Connector 270 includes a first opening 276 to receive interior inlet hose 268, a second opening 278 to receive first module hose 272, and a third opening 280 to receive second module hose 274. First and second module hoses 272, 274 each couple through a male coupler 282 to first and second valve modules 156, 158 respectively. In operation, air from air supply 152 travels through supply line 148, enters outer box line assembly 260 through exterior inlet hose 264 and passes through elbow 266 to interior inlet hose 268. The air then travels from inlet hose 268 to union tee connector 270 where the air is divided into first module hose 272 and second module hose 274. The air passes through first and second module hoses 272, 274 into first and second valve modules 156, 158 respectively. The operation of first and second valve modules 156, 158 is described below.

Control box 58 includes a base 284, a cover 286, and a tray 288. Cover 286 includes a plurality of fasteners (i.e., screws) 290. Base 284 includes a plurality of threaded cover posts 292. Cover posts 292 are configured to receive screws 290 to couple cover 286 to base 284. Cover 286 and base 284 define an inner region 298. Tray 288 couples to base 284 with a plurality of rivets 291 riveted through a plurality of rivet holes 293 located on tray 288 and base 284.

Inner box line assembly 262, first valve module 156, second valve module 158, control board 250, and multiplexer 252 are contained within inner region 298. Base 284 further includes a plurality of control board posts 294, a plurality of multiplexer posts 296, and a plurality of module posts 300. First and second valve modules 156, 158 are coupled to module posts 300 by shoulder screws 302 and washers 304. Control board 250 and multiplexer 252 are respectively coupled to control board posts 294 and multiplexer posts 296 by a plurality of snap mounts 306.

First and second valve modules 156, 158 attach to third air lines 150 a, b, d-f, and g-l through a plurality of couplers 308. Couplers 308 include a first end 310 and a second end 312. Third air lines 150 a, b, d-f, and g-l each include a fitting (not shown) receivable by second end 312. Each first end 310 mounts to a port 314 in first and second valve modules 156, 158. First end 310 mounts through a plurality of openings 316 in base 284.

A plurality of feedback couplers 318 mount through a plurality of feedback openings 320 in base 284. Feedback couplers 318 include a first feedback end 322 and a second feedback end 324. First feedback end 322 couples to a feedback line (not shown) that in turn couples to a feedback port 135 located on each air zone 160. Second feedback end 324 receives a feedback transfer line 326. Each transfer line 326 couples to a pressure transducer 328 located on the control board 250. Pressure transducer 328 receives the pressure from each air zone 160 and transmits to control unit 42 a pressure data signal representing the internal air pressure of the zone 160. Control unit 42 uses these pressure signals to determine the appropriate pressures for certain mattress functions such as CPR, patient transfer, and max-inflate. Pressure signals from the transducer 328 coupled to the foot zone 160k are also used to maintain optimal pressure in foot zone 160k. In the illustrated embodiment, pressure in foot zone 160k (zone 3) is computed as a percentage of the pressure in seat zone 160e (zone 2). The pressures in seat zone 160e and head zone 160f are determined using both the tranducers 328 and the pressure sensors 136. The pressures in one or more of the zones 160 may be adjusted in real time.

As shown in FIG. 23, fill valves 163a-l and vent valves 165a-l are coupled to various portions of patient support 10 through third air lines 150 a, b, d-f, and g-l. Fill valve 163a and vent valve 165a are coupled to upper foot bolsters 140c, fill valve 163b and vent valve 165b are coupled to lower side bolsters 142 a, b, fill valve 163c is coupled to atmosphere and vent valve 165c is reserved for future therapies. Also, fill valve 163d and vent valve 165d are coupled to first turn assist 74a, fill valve 163e and vent valve 165e are coupled to seat bladders 62, fill valve 163f and vent valve 165f are coupled to head bladder assembly 60, fill valve 163g and vent valve 165g are coupled to foot filler 80, fill valve 163h and vent valve 165h are coupled to upper side bolsters 140 a, b, fill valve 163i and vent valve 165i are coupled to deck filler 90, fill valve 163j and vent valve 165j are coupled to first turn assist 74b, fill valve 163k and vent valve 165k are coupled to foot bladders 164, fill valve 163l and vent valve 165l are coupled to lower foot bolsters 142c. Vent valves 165d, j are biased in the open position to vent air from first and second turn assist 74a, 74b when first and second turn assist 74a, 74b are not in use. Vent valves 165d, j return to their open position if the mattress loses power or pressure venting air from the first and second turn assist 74a, 74b. When air is vented from a zone 160, the pressure in the zone 160 after deflation is determined by the control system 42, 58 in real time rather than being predetermined.

In one embodiment, a user enters an input command to control unit 42. Control unit 42 processes the input command and transmits a control signal based on the input command through communication line 258 to control board 250. Additionally or alternatively, control signals could be based on operational information from control unit 42 to increase or decrease pressure within one or more of the zones 160 based on information obtained from transducers 328 and/or sensors 136.

It should be noted that in the illustrated embodiment, the mattress controls 42, 58 are independent from operation of the bed frame 4. In other embodiments, however, bed frame 4 and mattress 10 may be configured to exchange or share data through communication lines. For instance, data is communicated from bed frame 4 to mattress system 42, 58 and used to adjust support parameters of mattress 10. For instance, in one embodiment, a signal is transmitted from frame 4 when foot section 34 is retracting, so that mattress systems 42, 58 responds by decreasing internal pressure of vertical bladders 50 in foot assembly 64.

As described above, air supply 152 is capable of supplying air or acting as a vacuum to remove air from zones 160. While in supply mode, a microprocessor on control board 250 actuates corresponding fill valve 163a-1 or vent valve 165a-1 based on the control signal from control unit 42. For example, if the control signal indicates the pressure in head bladder assembly 160 is to be increased fill valve 163f is actuated. However, if the control signal indicates the pressure in head bladder assembly 160 is to be decreased vent valve 165f is actuated. While in vacuum mode one or more fill valves 163a-1 may be actuated to allow for rapid removal of air within the corresponding zones.

The present invention has been described with reference to certain exemplary embodiments, variations, and applications. However, the present invention is defined by the appended claims and therefore should not be limited by the described embodiments, variations, and applications.

The invention claimed is:

1. A patient support, comprising:
a cover including an interior region defined by a top portion and a bottom portion spaced from the top portion,
a base positioned between the top portion and the bottom portion of the cover, the base having a head end, a foot end, a longitudinal length extending from the head end to the foot end, and a width extending substantially perpendicular to the longitudinal length,
a plurality of inflatable bladders located between the base and the top portion of the cover, including at least a first can-shaped bladder and a second can-shaped bladder positioned adjacent to one another transversely across the width of the base, and a separable layer including at least one sensor configured to measure pressure applied to one or more of the can-shaped bladders, the at least one sensor being located externally to the base and the at least one sensor being located externally to the bladders and the at least one sensor being located within the interior region of the cover.

2. The patient support of claim 1, wherein the can-shaped bladders have a bottom circumference, vertical walls extending uprightly from the base toward the top portion of the cover and a circular top coupled to the vertical walls, the circular top having a circumference less than or equal to the bottom circumference of the bladder.

3. The patient support of claim 2, wherein the can-shaped bladders have a diameter in the range of about 3.5 inches.

4. The patient support of claim 3, wherein each pressure sensor is located underneath at least one bladder.

5. The patient support of claim 1, further comprising a second pressure sensing assembly operably coupled to the bladders to directly sense internal bladder inflation pressures.

6. The patient support of claim 5, further comprising a control unit configured to adjust internal bladder inflation pressure of one or more of the bladders in response to applied pressure data received from the pressure sensing assembly.

7. The patient support of claim 6, wherein the control unit is configured to adjust internal bladder pressure in response to internal bladder pressure data received from the second pressure sensing assembly.

8. The patient support of claim 1, further comprising a valve assembly operably coupled to the bladders to inflate and deflate the bladders, wherein the valve assembly is located between the base and the bottom portion of the cover.

9. The patient support of claim 1, wherein at least one of the sensors measures changes in intensity of light energy diffused in the pressure sensor in response to pressure applied to the patient support.

10. The patient support of claim 1, wherein the base includes a head section, a seat section, and a foot section positioned substantially end-to-end along the longitudinal length of the base from the head end to the foot end, further comprising an angle sensor located proximate the head section and configured to detect a change in the angle of the head section and configured to send a signal indicative of an angle of elevation of the head section to a control board located within the cover.

11. The patient support of claim 1, wherein the base includes a head section, a seat section, and a foot section, the head, seat and foot sections being aligned along the longitudinal length of the base from the head end to the foot end, each of the head, seat and foot sections includes at least one zone of inflatable bladders, and at least one of the bladder zones are independently inflatable.

12. The patient support of claim 11, wherein at least one of the bladder zones includes can-shaped bladders.

13. The patient support of claim 12, wherein the foot section includes can-shaped bladders.

* * * * *